(12) United States Patent
Poppe et al.

(10) Patent No.: US 11,419,743 B2
(45) Date of Patent: Aug. 23, 2022

(54) MOTORIZED TELESCOPING MEDICAL DEVICE DELIVERY SYSTEM WITH MECHANICAL BAILOUT FEATURE

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Bradley S. Swehla, Eagan, MN (US); Christopher Jay Scheff, Elk River, MN (US); Eric Gagner, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 633 days.

(21) Appl. No.: 16/507,167

(22) Filed: Jul. 10, 2019

(65) Prior Publication Data
US 2020/0015968 A1    Jan. 16, 2020

Related U.S. Application Data

(60) Provisional application No. 62/696,415, filed on Jul. 11, 2018.

(51) Int. Cl.
*A61F 2/966* (2013.01)
*A61F 2/24* (2006.01)
(Continued)

(52) U.S. Cl.
CPC ............ *A61F 2/966* (2013.01); *A61F 2/2436* (2013.01); *A61M 25/0113* (2013.01);
(Continued)

(58) Field of Classification Search
CPC ...... A61F 2/2427; A61F 2/966; A61F 2/2436; A61F 2/243; A61F 2/2439;
(Continued)

(56) References Cited

U.S. PATENT DOCUMENTS

| 5,800,526 A | 9/1998 | Anderson et al. |
| 6,231,561 B1 | 5/2001 | Frazier et al. |

(Continued)

FOREIGN PATENT DOCUMENTS

| CN | 1399571 A | 2/2003 |
| CN | 203226856 U | 10/2013 |

(Continued)

OTHER PUBLICATIONS

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
(Continued)

*Primary Examiner* — Kelly J Bekker
*Assistant Examiner* — Mikail A Mannan
(74) *Attorney, Agent, or Firm* — Seager, Tufte & Wickhem LLP

(57) ABSTRACT

A system for delivering an implantable medical device includes an outer sheath drive assembly and an actuation shaft drive assembly. The outer sheath drive assembly is configured to cause an outer sheath to translate relative to a handle, and includes an outer sheath drive motor. The actuation shaft drive assembly is configured to cause an actuation shaft to translate relative to the handle, and includes an actuation shaft drive motor. The outer sheath drive motor and/or the actuation shaft drive motor may be removed from the system, and the outer sheath drive assembly and/or the actuation shaft drive assembly may instead be manually driven.

20 Claims, 23 Drawing Sheets

(51) Int. Cl.
 *A61M 25/01* (2006.01)
 *A61M 39/10* (2006.01)
(52) U.S. Cl.
 CPC ........ *A61M 25/0136* (2013.01); *A61M 39/10* (2013.01); *A61M 2039/1033* (2013.01)
(58) Field of Classification Search
 CPC ...... A61F 2002/9505; A61F 2002/9511; A61F 2002/9583; A61F 2/95; A61F 2/9517; A61F 2/962; A61B 2017/1205; A61B 2017/12095; A61B 2017/00623; A61M 25/0113; A61M 25/0136; A61M 39/10; A61M 2039/1033
 See application file for complete search history.

(56) References Cited

U.S. PATENT DOCUMENTS

| | | | |
|---|---|---|---|
| 7,727,189 | B2 | 6/2010 | VanTassel et al. |
| 7,748,389 | B2 | 7/2010 | Salahieh et al. |
| 7,972,359 | B2 | 7/2011 | Kreidler |
| 8,221,384 | B2 | 7/2012 | Frazier et al. |
| 8,372,143 | B2 | 2/2013 | Majercak et al. |
| 8,562,509 | B2 | 10/2013 | Bates |
| 2003/0208214 | A1 | 11/2003 | Loshakove et al. |
| 2004/0117004 | A1 | 6/2004 | Osborne et al. |
| 2004/0220682 | A1 | 11/2004 | Levine et al. |
| 2005/0025621 | A1 | 2/2005 | Horng et al. |
| 2005/0125020 | A1 | 6/2005 | Meade et al. |
| 2009/0005803 | A1 | 1/2009 | Batiste |
| 2009/0099596 | A1 | 4/2009 | McGuckin, Jr. et al. |
| 2009/0099638 | A1 | 4/2009 | Grewe |
| 2010/0016953 | A1 | 1/2010 | Sisken et al. |
| 2011/0054515 | A1 | 3/2011 | Bridgeman et al. |
| 2012/0172654 | A1 | 7/2012 | Bates |
| 2012/0245619 | A1 | 9/2012 | Guest et al. |
| 2013/0231735 | A1* | 9/2013 | Deem ..................... A61F 2/95 623/2.11 |
| 2014/0005676 | A1 | 1/2014 | Shelton, IV et al. |
| 2014/0188157 | A1 | 7/2014 | Clark |
| 2014/0343670 | A1 | 11/2014 | Bakis |
| 2015/0005809 | A1 | 1/2015 | Tyres et al. |
| 2017/0135748 | A1 | 5/2017 | Aldridge et al. |
| 2017/0156840 | A1 | 6/2017 | Edmiston et al. |
| 2018/0153689 | A1* | 6/2018 | Maimon ............... A61F 2/2418 |

FOREIGN PATENT DOCUMENTS

| | | |
|---|---|---|
| EP | 1595504 A1 | 11/2005 |
| EP | 2481381 A1 | 8/2012 |
| JP | 2003532457 A | 11/2003 |
| JP | 2005324019 A | 11/2005 |
| JP | 2007513684 A | 5/2007 |
| WO | 0035352 A1 | 6/2000 |
| WO | 0121247 A1 | 3/2001 |
| WO | 0170119 A1 | 9/2001 |
| WO | 03032818 A2 | 4/2003 |
| WO | 2007044536 A2 | 4/2007 |
| WO | 2010148246 A2 | 12/2010 |
| WO | 2013126529 A2 | 8/2013 |
| WO | 2014106239 A1 | 7/2014 |

OTHER PUBLICATIONS

International Search Report and Written Opinion dated Apr. 22, 2014 for International Application No. PCT/US2013/078454, see p. 1-13.

Aryana et al., "Incomplete Closure of the Left Atrial Appendage: Implication and Management." Curr Cardiol Rep., 18(9):82, 2016, see pp. 1-7.

Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.

University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019, see p. 1.

Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

International Search Report and Written Opinion dated Jun. 28, 2019 for International Application No. PCT/US2019/023807, see p. 1-14.

International Search Report and Written Opinion dated Oct. 2, 2019 for International Application No. PCT/US2019/041147, see p. 1-13.

\* cited by examiner

MOTORIZED TELESCOPING MEDICAL DEVICE DELIVERY SYSTEM WITH MECHANICAL BAILOUT FEATURE

CROSS-REFERENCE TO RELATED APPLICATIONS

This application claims the benefit of priority under 35 U.S.C. § 119 to U.S. Provisional Application Ser. No. 62/696,415, filed Jul. 11, 2018, the entirety of which is incorporated herein by reference.

TECHNICAL FIELD

The present disclosure pertains to medical device delivery systems. More particularly, the present disclosure pertains to medical device delivery systems that include one or more motors actuating a telescoping assembly to deliver and deploy a medical device as well as a mechanical bailout feature.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example system for delivering an implantable medical device includes a handle housing that extends from a proximal region to a distal region and an outer sheath access door that is disposed near the proximal region. An outer sheath that is configured to cover at least a portion of the implantable medical device extends distally from the handle housing. An outer sheath coupler is disposed within the handle housing and is secured to the outer sheath, with an outer sheath nut threadedly disposed on an outer sheath threaded rod and operably coupled to the outer sheath coupler. An outer sheath drive motor is operably coupled to the outer sheath threaded rod such that actuation of the outer sheath drive motor causes the outer sheath threaded rod to rotate relative to the outer sheath nut, thereby causing the outer sheath nut to translate relative to the outer sheath threaded rod as the outer sheath nut is held against rotation, and thus causing the outer sheath coupler and the outer sheath to translate relative to the handle housing. The outer sheath drive motor is configured to be disengaged from the outer sheath threaded rod upon removal of the outer sheath access door such that a manual drive tool can be used to engage and manually rotate the outer sheath threaded rod.

Additionally or alternatively, the outer sheath threaded rod may include a keyed aperture at an end thereof, and the outer sheath drive motor may include a keyed drive shaft that is complementary to the keyed aperture and is slidingly engageable therewith.

Additionally or alternatively, the keyed aperture may include a splined aperture, and the keyed drive shaft may include a splined drive shaft.

Additionally or alternatively, the outer sheath access door may extend along a side of the handle housing such that removal of the outer sheath access door exposes at least a portion of a length of the outer sheath drive motor.

Additionally or alternatively, the outer sheath access door may have a snap-fit connection with the handle housing.

Additionally or alternatively, the outer sheath access door may be disposed on a proximal end of the handle housing.

Additionally or alternatively, the system may further include a motor carrier operably coupled to the outer sheath drive motor such that removal of the motor carrier through the outer sheath access door removes the outer sheath drive motor.

Additionally or alternatively, the motor carrier may be operably coupled to the outer sheath access door such that removal of the outer sheath access door removes the motor carrier from within the handle housing.

Additionally or alternatively, the system may further include an actuation shaft that extends within the outer sheath. An actuation shaft coupler may be secured to the actuation shaft such that translation of the actuation shaft coupler relative to the handle housing causes translation of the actuation shaft relative to the handle housing. An actuation shaft nut may be threadedly disposed on an actuation shaft threaded rod and operably coupled to the actuation shaft coupler. An actuation shaft drive motor may be operably coupled to the actuation shaft threaded rod such that actuation of the actuation shaft drive motor causes the actuation shaft threaded rod to rotate relative to the actuation shaft nut, thereby causing the actuation shaft nut to translate relative to the actuation shaft threaded rod as the actuation shaft nut is held against rotation, and thus causing the actuation shaft coupler and the actuation shaft to translate relative to the handle housing. The actuation shaft drive motor may be configured to be disengaged from the second threaded rod upon removal of the actuation shaft access door such that the manual drive tool can be used to manually rotate the actuation shaft threaded rod.

Additionally or alternatively, the actuation shaft threaded rod may include a keyed aperture at an end thereof, and the actuation shaft drive motor may include a keyed drive shaft that is complementary to the keyed aperture and is slidingly engageable therewith.

Additionally or alternatively, the keyed aperture may include a splined aperture, and the keyed drive shaft may include a splined drive shaft.

Additionally or alternatively, the actuation shaft access door may extend along a side of the handle housing such that removal of the actuation shaft access door exposes at least a portion of a length of the actuation shaft drive motor.

Additionally or alternatively, the actuation shaft access door may have a snap-fit connection with the handle housing.

Another system for delivering an implantable device includes a handle housing having an outer sheath access door. An outer sheath is configured to cover at least a portion of the implantable medical device and an outer sheath coupler is secured to the outer sheath such that translation of the outer sheath coupler relative to the handle housing causes translation of the outer sheath relative to the handle housing. An outer sheath nut is threadedly disposed on a threaded rod and is operably coupled to the outer sheath coupler. An outer sheath drive motor is operably coupled to the threaded rod such that actuation of the outer sheath drive motor causes the threaded rod to rotate relative to the outer sheath nut, thereby causing the outer sheath nut to translate relative to the threaded rod as the outer sheath nut is held against rotation, and thus causes the outer sheath coupler and the outer sheath to translate relative to the handle housing. The outer sheath drive motor is configured to be disengaged from the threaded rod upon removal of the outer sheath access door. An outer sheath drive tool has an engagement end and a handle end, the engagement end being configured to engage the threaded rod once the outer sheath drive motor has been removed so that the threaded rod can be manually rotated.

Additionally or alternatively, the outer sheath threaded rod may include a keyed aperture at an end thereof, and the outer sheath drive motor may include a keyed drive shaft that is complementary to the keyed aperture and is slidingly engageable therewith.

Additionally or alternatively, the keyed aperture may include a splined aperture, and the keyed drive shaft may include a splined drive shaft.

Another system for delivering an implantable medical device includes a handle housing having an access door. An outer sheath that is configured to cover at least a portion of the implantable device extends distally from the handle housing. An outer sheath coupler is disposed within the handle housing and is secured to the outer sheath. An outer sheath nut is threadedly disposed on an outer sheath threaded rod and is operably coupled to the outer sheath coupler. An outer sheath drive motor is operably coupled to the outer sheath threaded rod such that actuation of the outer sheath drive motor causes the outer sheath threaded rod to rotate relative to the outer sheath nut, thereby causing the outer sheath nut to translate relative to the outer sheath threaded rod as the outer sheath nut is held against rotation, and thus causing the outer sheath coupler and the outer sheath to translate relative to the handle housing. An actuation shaft extends within the outer sheath and is operably coupled to translation members secured relative to the implantable medical device such that translation of the actuation shaft causes translation of the translation members which in turn causes the implantable medical device to shift from a delivery configuration to a deployment configuration. An actuation shaft coupler is secured to the actuation shaft such that translation of the actuation shaft coupler relative to the handle housing causes translation of the actuation shaft relative to the handle housing. An actuation shaft nut is threadedly disposed on an actuation shaft threaded rod and is operably coupled to the actuation shaft coupler. An actuation shaft drive motor is operably coupled to the actuation shaft threaded rod such that actuation of the actuation shaft drive motor causes the actuation shaft threaded rod to rotate relative to the actuation shaft nut, thereby causing the actuation shaft nut to translate relative to the actuation shaft threaded rod as the actuation shaft nut is held against rotation, causing the actuation shaft coupler and the actuation shaft to translate relative to the handle housing. Removal of the access door enables removal of the outer sheath drive motor.

Additionally or alternatively, the system may further include a manual drive tool including an outer sheath drive shaft configured to rotatably engage the outer sheath threaded rod in place of the outer sheath drive motor and an actuation shaft drive shaft configured to rotatably engage the actuation shaft threaded rod at an end thereof opposite that of the actuation shaft drive motor.

Additionally or alternatively, the manual drive tool may be configured to maintain a drive ratio between the outer sheath drive shaft and the actuation shaft drive shaft.

Additionally or alternatively, the access door may be configured to be manually removed from the handle housing.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
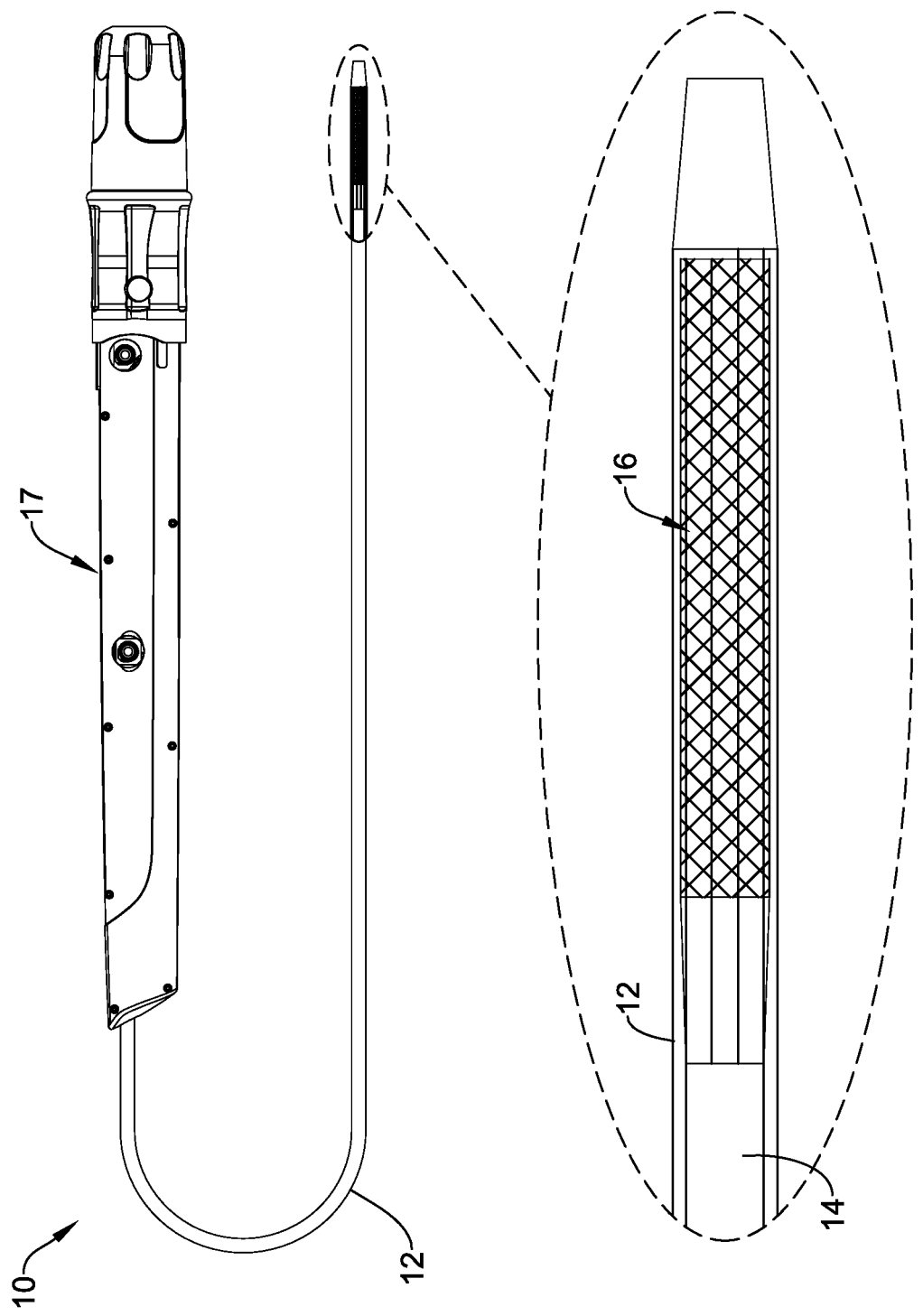
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the body. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed. For example, therapies have been developed which allow a blocked coronary artery to be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16 (shown in the detailed view of FIG. 1), such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, one or more tubular members (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1, for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system (e.g., the medical device system 10) may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
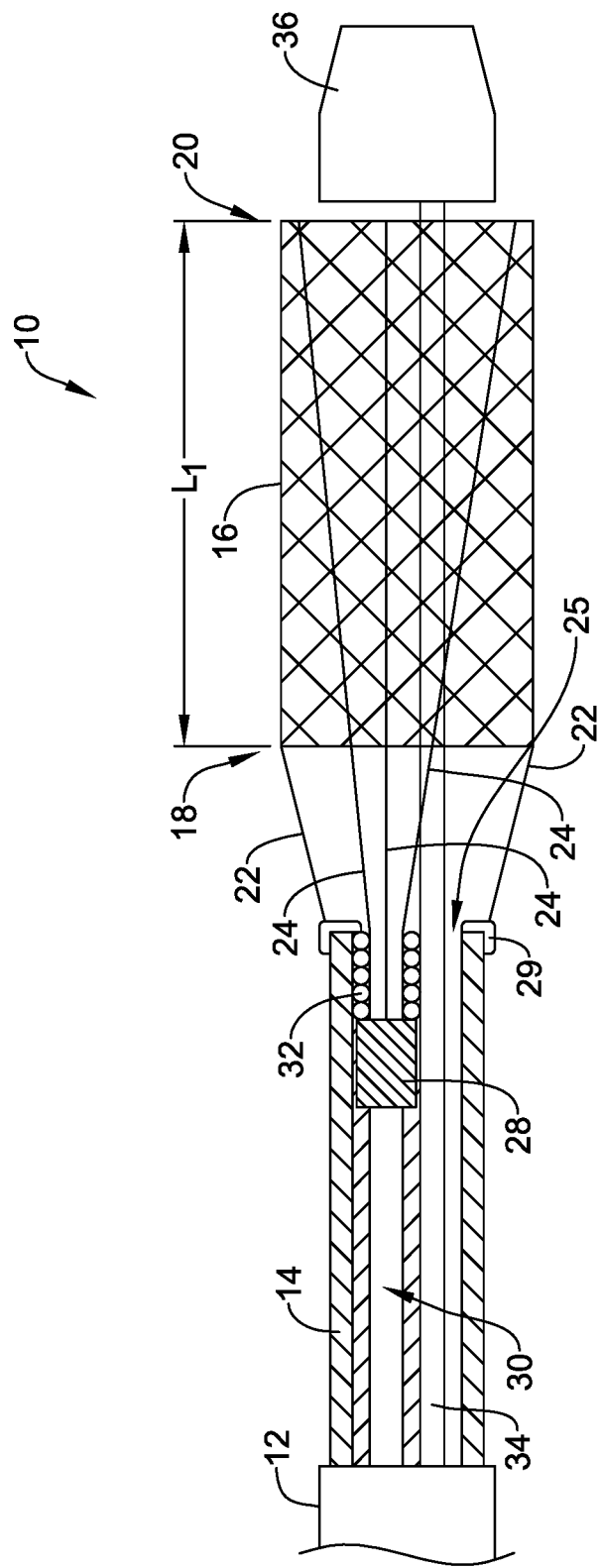
FIG. 2 is a partial cross-sectional view of a portion of the example medical device delivery system of FIG. 1.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially-deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially-deployed position after the outer sheath 12 has been retracted to uncover the implant 16. For example, FIG. 2 illustrates that the support members 22 may be designed such that the distal end of each of the support members 22 may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 29 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to-proximal direction such that the translation of the translation members (via operator manipulation at the handle, for example) may "pull" the distal end 20 of the implant closer to the proximal end 18 of the implant 16.

Figure 3:
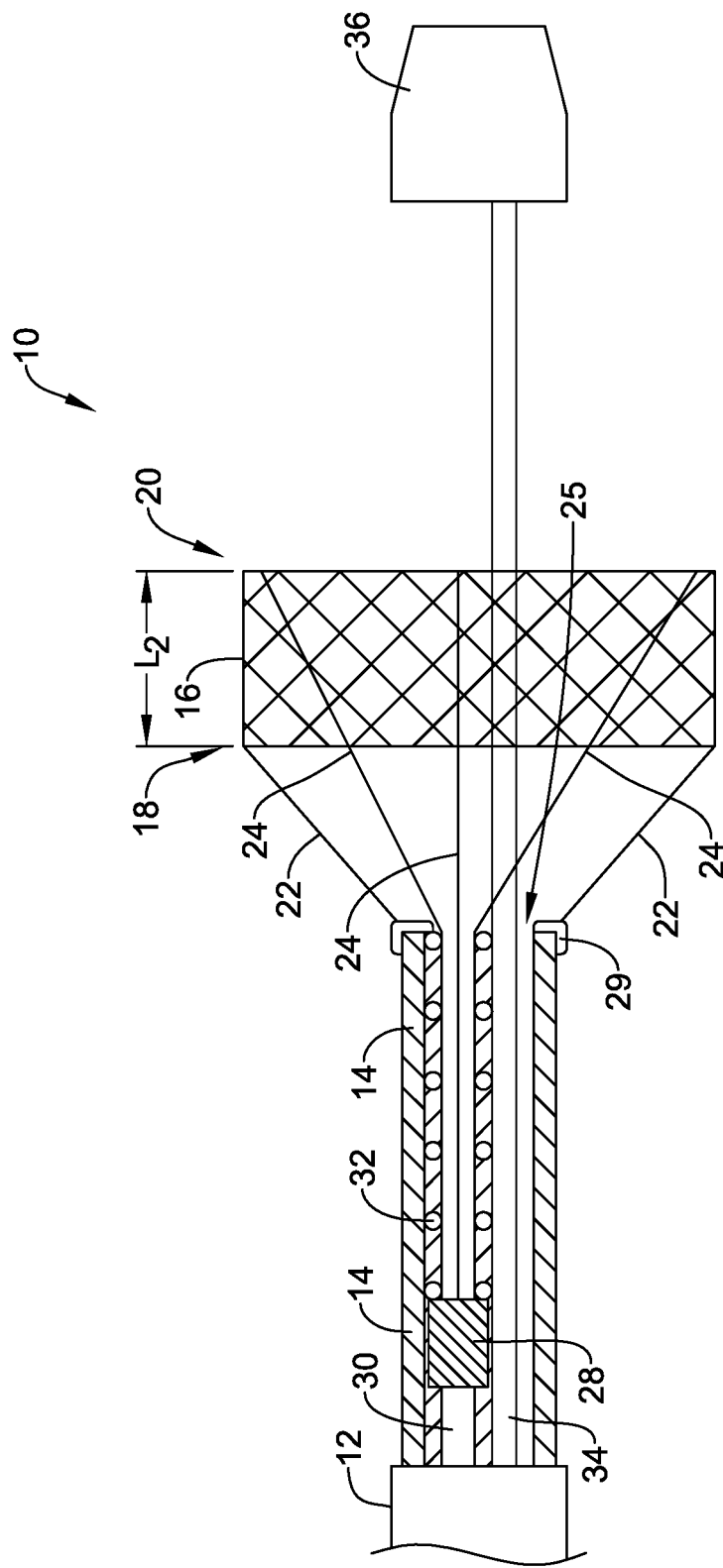
FIG. 3 is a partial cross-sectional view of a portion of the example medical device delivery system of FIG. 1.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as "$L_2$", whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, the implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16 described herein.

In some examples, an operator may be able to manipulate the translation members 24 via the handle 17. For example, the handle 17 may include an actuation member designed to control the translation of the translation members 24. FIG. 2 illustrates that the handle member 17 may be coupled to the translation members 24 via an actuation shaft 30 and a coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner catheter 14 from the coupling member 28 to the handle member 17.

For purposes of discussion herein, the inner catheter 14 may also be referred to as an inner member or liner 14. The liner 14 may include a number of different features shown in the figures described herein. For example, the liner 14 may include a lumen 25. Further, the translation members 24, coupler 28, actuation shaft 30, tubular guidewire member 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil 32 maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil 32 may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may include a lumen which permits a guidewire to extend and translate therein. In other words, the medical device system 10 may be advanced to a target site within a body over a guidewire extending within the lumen of the tubular guidewire member 34. Further, the tubular guidewire member 34 may extend from the handle member 17, through the lumen 25 of the inner member 14, through the implant 16 and terminate at a nosecone 36.

Figure 4:
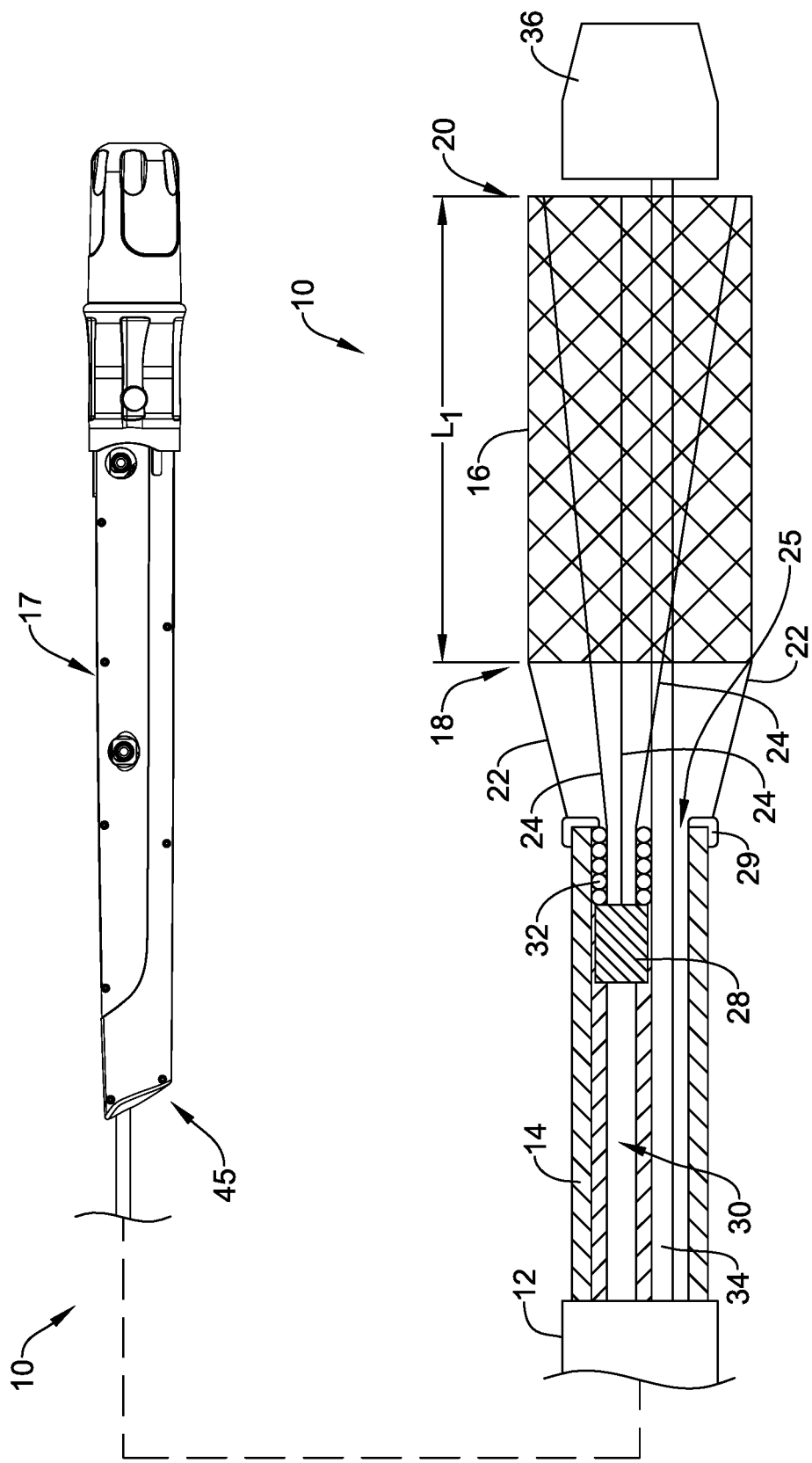
FIG. 4 is a partial cross-sectional view of the example medical device delivery system of FIG. 1.

It can be appreciated from the above discussion that the outer member 12, the inner shaft 14, the actuation shaft 30 (which is coupled to the translation members 24) and the tubular guidewire member 34 may all extend from a position adjacent the medical implant 16 to a position in which they enter the handle member 17. For example, FIG. 4 shows that the outer sheath 12, the inner shaft 14, the actuation shaft 30 (which is coupled to the translation members 24) and the tubular guidewire member 34 may extend from an example medical implant 16 (which may be similar in form and function to the medical implant described above) and enter a distal end 45 of the handle member 17.

Figure 5:
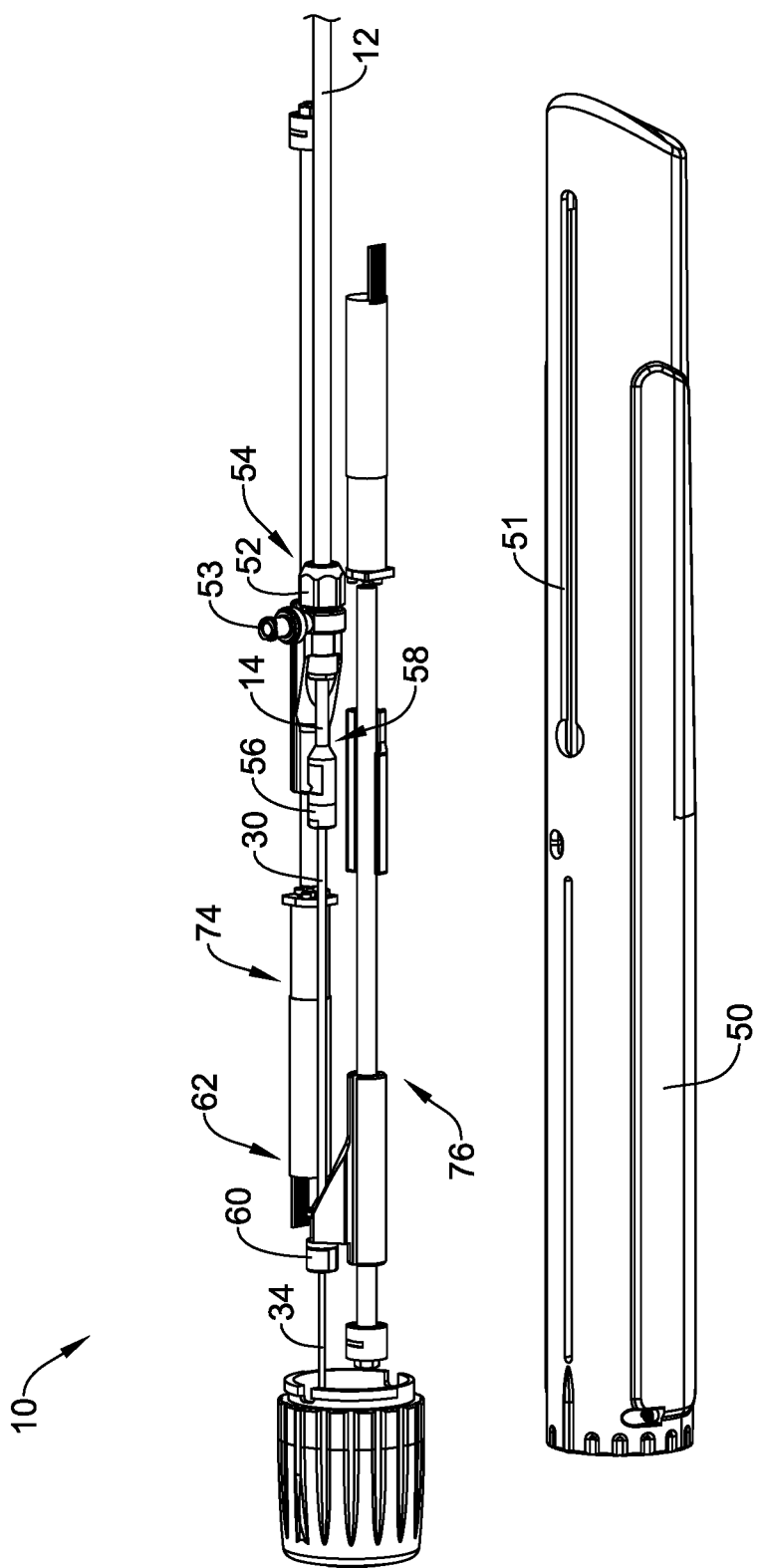
FIG. 5 is an exploded view of the example medical device delivery system of FIG. 1.
Figure 6:
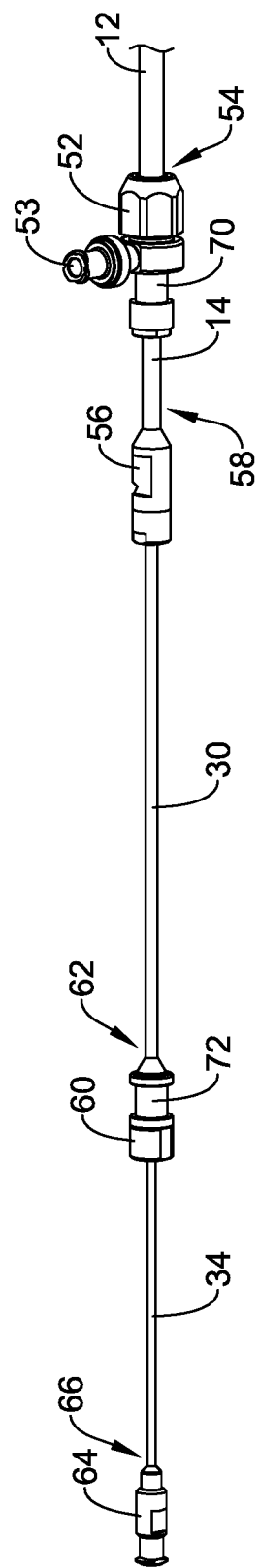
FIG. 6 is a view of a portion of the example medical device delivery system of FIG. 1.

FIG. 5 shows the medical device system 10 with a housing portion 50 shown removed to reveal features of the handle 17. FIG. 6 further illustrates the coaxial and telescoping arrangement between the guidewire member 34, the actuation shaft 30, the inner catheter 14 and the outer sheath 12. Within the handle 17, an outer sheath coupler 52 is operably secured to a proximal end 54 of the outer sheath 12 such that the outer sheath 12 moves relative to the handle 17 when the outer sheath coupler 52 moves relative to the housing portion 50. In some cases, the outer sheath coupler 52 may include a luer lock flushing port 53, and the housing portion 50 may include an elongate slot 51 in order to accommodate movement of the outer sheath coupler 52 (and hence movement of the luer lock flushing port 53) relative to the handle 17.

A coupler 56 may be secured to a proximal end 58 of the inner catheter 14. In some cases, the coupler 56 may be fixed in place within the handle 17. An actuation shaft coupler 60 may be operably coupled to a proximal end 62 of the actuation shaft 30 such that the actuation shaft 30 moves relative to the handle 17 when the actuation shaft coupler 60 moves relative to the handle 17. A coupler 64 may be secured to a proximal end 66 of the guidewire member 34. In some cases, the coupler 64 may be fixed in place within the handle 17.

In some cases, as can be seen in FIG. 6, the outer sheath coupler 52 may include an annular recess 70 and the actuation shaft coupler 60 may include an annular recess 72. In some cases, as will be discussed, the annular recess 70 and the annular recess 72 may permit coupling the outer sheath coupler 52 and the actuation shaft coupler 60 with an outer sheath drive assembly 74 and an actuation shaft drive assembly 76, respectively. In some cases, as will be appreciated, the outer sheath drive assembly 74 may be configured to cause the outer sheath coupler 52, and hence the outer sheath 12, to translate relative to the handle 17. The actuation shaft drive assembly 76 may be configured to cause the actuation shaft coupler 60, and hence the actuation shaft 30, to translate relative to the handle 17. The outer sheath drive assembly 74 is better illustrated in FIG. 7 and the actuation shaft drive assembly 76 is better illustrated in FIG. 8.

Figure 7:
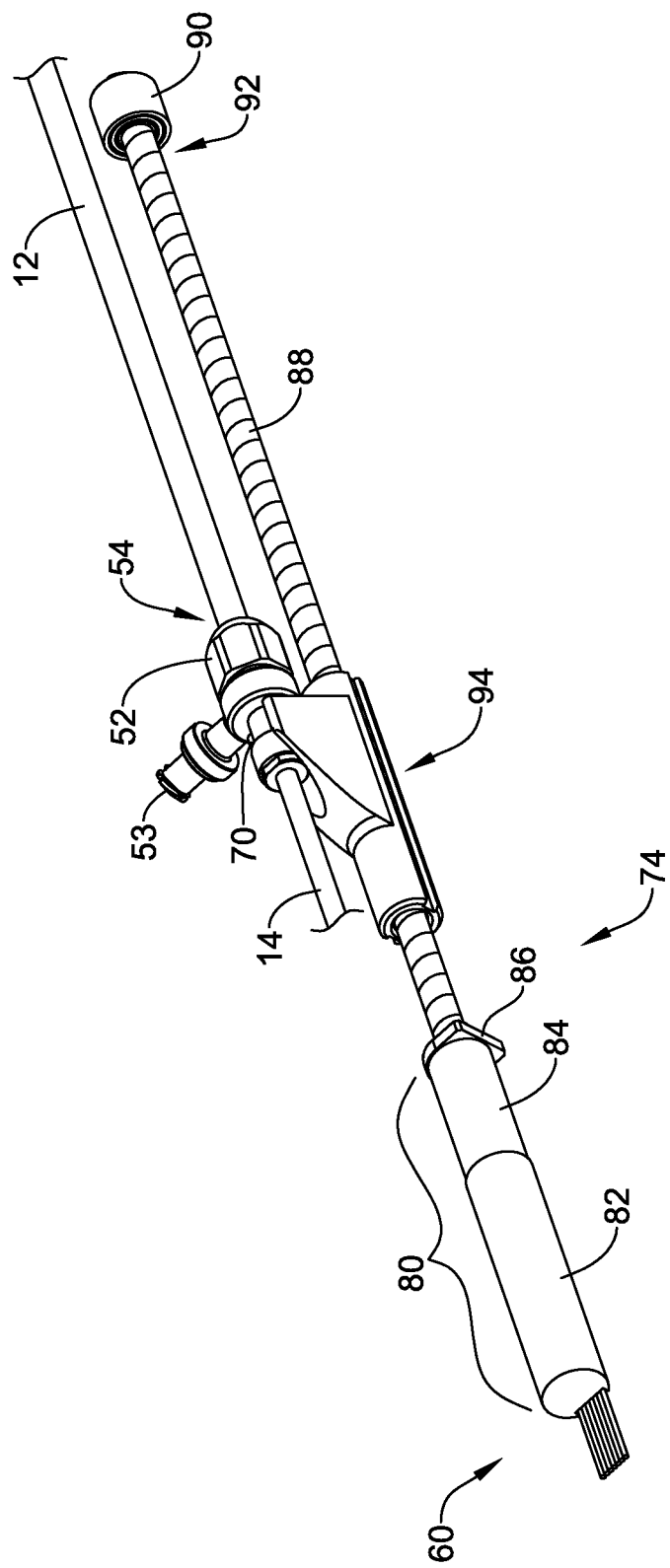
FIG. 7 is a view of a portion of the example medical device delivery system of FIG. 1.

As seen in FIG. 7, the outer sheath drive assembly 74 includes an outer sheath drive assembly motor 80. In some cases, the outer sheath drive assembly motor 80 includes a motor 82 and a gear box 84, although in some cases the motor 82 may be a direct drive motor without a separate gear box. In some cases, the outer sheath drive assembly motor 80 includes a motor coupling 86 by which the outer sheath drive assembly motor 80 is operably coupled to an outer sheath drive assembly threaded rod 88. In some instances, the outer sheath drive assembly threaded rod 88 may instead be formed as an integral part of an output shaft of the motor 82. When the outer sheath drive assembly motor 80 is actuated, the outer sheath drive assembly threaded rod 88 is driven into rotation. A thrust bearing 90 accepts a remote end 92 of the outer sheath drive assembly threaded rod 88, and is configured to permit the outer sheath drive assembly threaded rod 88 to rotate relative to the thrust bearing 90. An outer sheath nut 94 is threadedly disposed on the outer sheath drive assembly threaded rod 88 and is held against rotation by virtue of being engaged with the outer sheath coupler 52. As the outer sheath drive assembly threaded rod 88 rotates, the outer sheath nut 94 translates relative to the outer sheath drive assembly threaded rod 88, and as a result, the outer sheath 12 translates relative to the handle 17.

Figure 8:
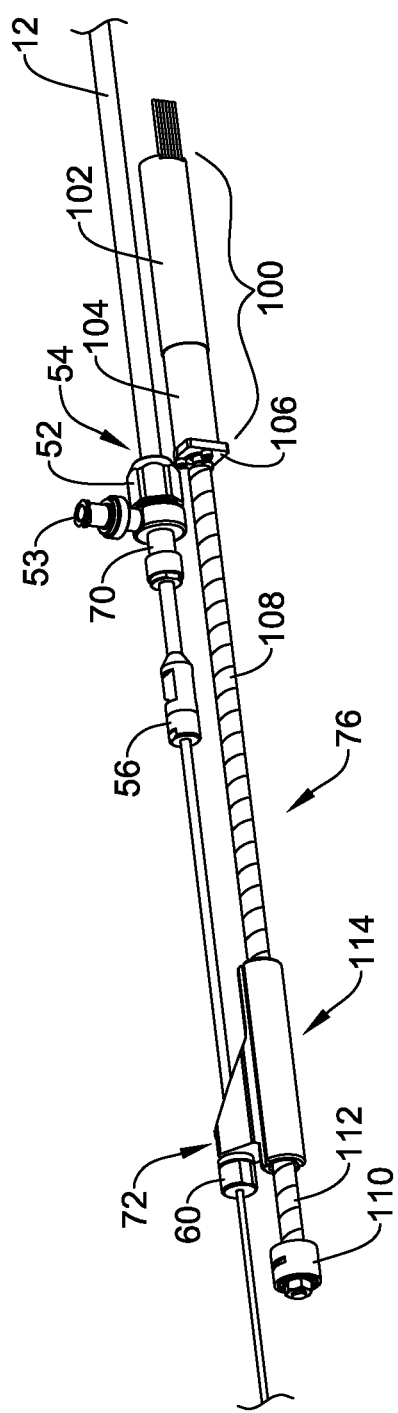
FIG. 8 is a view of a portion of the example medical device delivery system of FIG. 1.

As seen in FIG. 8, the actuation shaft drive assembly 76 includes an actuation shaft drive assembly motor 100. In some cases, the actuation shaft drive assembly motor 100 includes a motor 102 and a gear box 104, although in some cases the motor 102 may be a direct drive motor without a separate gear box. In some cases, the actuation shaft drive assembly motor 100 includes a motor coupling 106 by which the actuation shaft drive assembly motor 100 is operably coupled to an actuation shaft drive assembly threaded rod 108. In some instances, the actuation shaft drive assembly threaded rod 108 may instead be formed as an integral part of an output shaft of the motor 102. When the actuation shaft drive assembly motor 100 is actuated, the actuation shaft drive assembly threaded rod 108 is driven into rotation. A thrust bearing 110 accepts a remote end 112 of the actuation shaft drive assembly threaded rod 108, and is configured to permit the actuation shaft drive assembly threaded rod 108 to rotate relative to the thrust bearing 110. An actuation shaft nut 114 is threadedly disposed on the actuation shaft drive assembly threaded rod 108 and is held against rotation by virtue of being engaged with the actuation shaft coupler 60. As the actuation shaft drive assembly threaded rod 108 rotates, the actuation shaft nut 114 translates relative to the actuation shaft drive assembly threaded rod 108, and as a result, the actuation shaft 30 translates relative to the handle 17.

FIGS. 1 through 8 describe a number of features of the medical device system 10, in which the outer sheath drive assembly 74 includes the outer sheath drive assembly motor 80 for translating the outer sheath 12 relative to the handle 17 and in which the actuation shaft drive assembly 76 includes the actuation shaft drive assembly motor 100 for translating the actuation shaft 30 relative to the handle 17. In some cases, there may be a desire to instead be able to actuate the outer sheath drive assembly 74 and/or the actuation shaft drive assembly 76 manually. For example, if a power supply were to fail within the medical device system 10, or if the outer sheath drive assembly motor 80 and/or the actuation shaft drive assembly motor 100 were to fail during delivery and/or implantation of the implantable medical device 16, it may be beneficial to have a way to manually advance or withdraw the outer sheath 12 and/or the actuation shaft 30 in order to either finish implanting the implantable medical device 16 or to prepare the implantable medical device 16 to be withdrawn from the patient still secured within the medical device system 10. FIGS. 9 through 12 show an example of how the outer sheath drive assembly motor 80 may be removed for manual actuation of the outer sheath drive assembly threaded rod 88 and FIGS. 13 through 16 show an example of how the actuation shaft drive assembly motor 100 may be removed for manual actuation of the actuation shaft drive assembly threaded rod 108.

Figure 9:
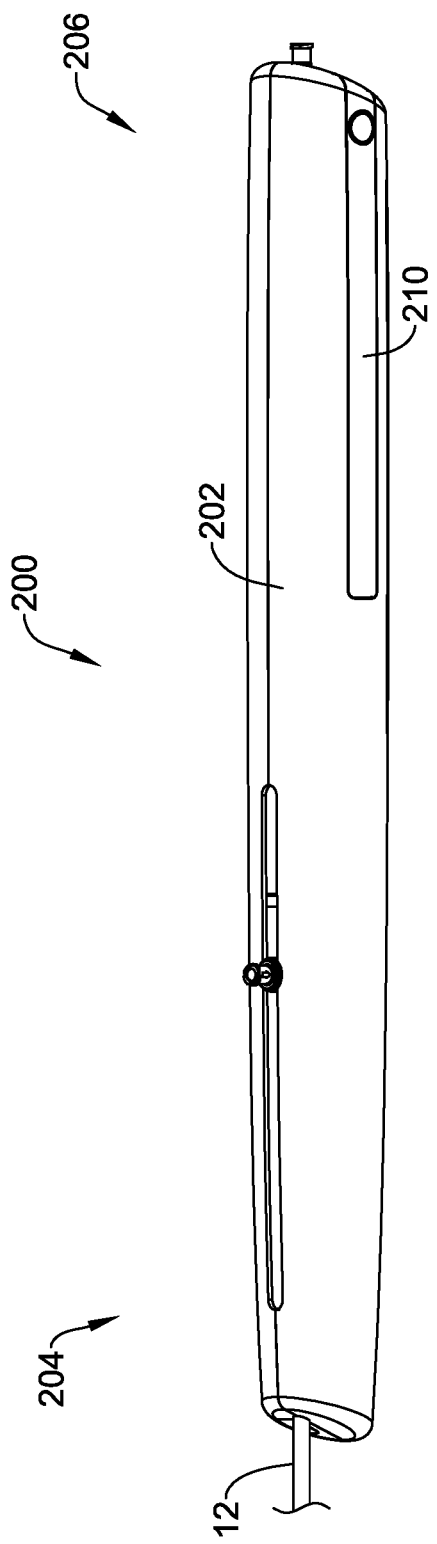
FIG. 9 is a side view of an example medical device system.
Figure 10:
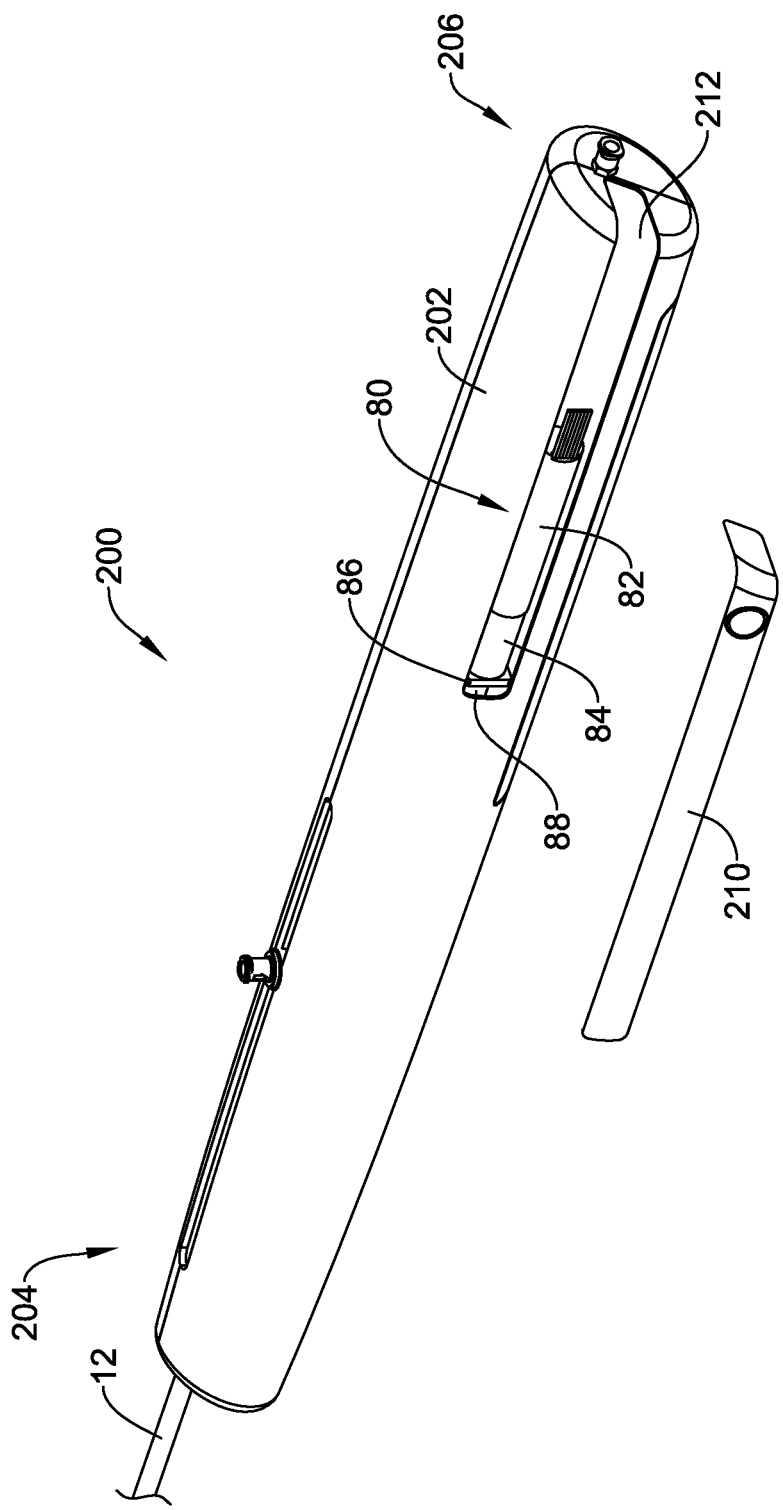
FIG. 10 is a partially exploded view of the example medical device system of FIG. 9.

FIG. 9 shows the proximal portion of a medical device system 200. As can be seen, the medical device system 200 includes a handle 202 that extends from a distal region 204 to a proximal region 206. While a detailed look at what is inside the handle 202 is not provided, it is appropriate to consider what is inside the handle 202 to be the same as, or equivalent to, what is shown in the previous FIGS. For example, the medical device system 200 includes the outer sheath drive assembly 74 as well as the actuation shaft drive assembly 76, as well as the telescoping arrangement between the actuation shaft 30 and the outer sheath 12. As seen in FIG. 9, the handle 202 includes an outer sheath access door 210. In some cases, the outer sheath access door 210 may have a snap-fit connection to the handle 202. In some instances, fingers or a tool may be used to remove the outer sheath access door 210. Removing the outer sheath access door 210, as shown for example in FIG. 10, reveals an outer sheath cavity 212, with the outer sheath drive assembly motor 80. Also visible in FIG. 10 is the outer sheath motor coupling 86, which enables the outer sheath assembly drive motor 80 to engage the outer sheath drive assembly threaded rod 88.

If necessary, such as in the case of power loss, motor failure, or other mechanical failures, the outer sheath assembly drive motor 80 may be removed once the outer sheath access door 210 has been removed from the handle 202. This can be seen for example in FIG. 11, where both the outer sheath access door 210 as well as the outer sheath assembly drive motor 80 has been removed from the handle 202. In some cases, the outer sheath assembly drive motor 80 may be held against translational movement by a fixation feature present within the outer sheath cavity 212 and/or within the outer sheath access door 210, and the outer sheath assembly drive motor 80 may be released from the fixation feature by sliding the outer sheath assembly drive motor 80 axially away from the fixation feature. In some cases, the outer sheath access door 210, when in place on the handle 202, prevents the outer sheath assembly drive motor 80 from being moved axially.

Figure 11:
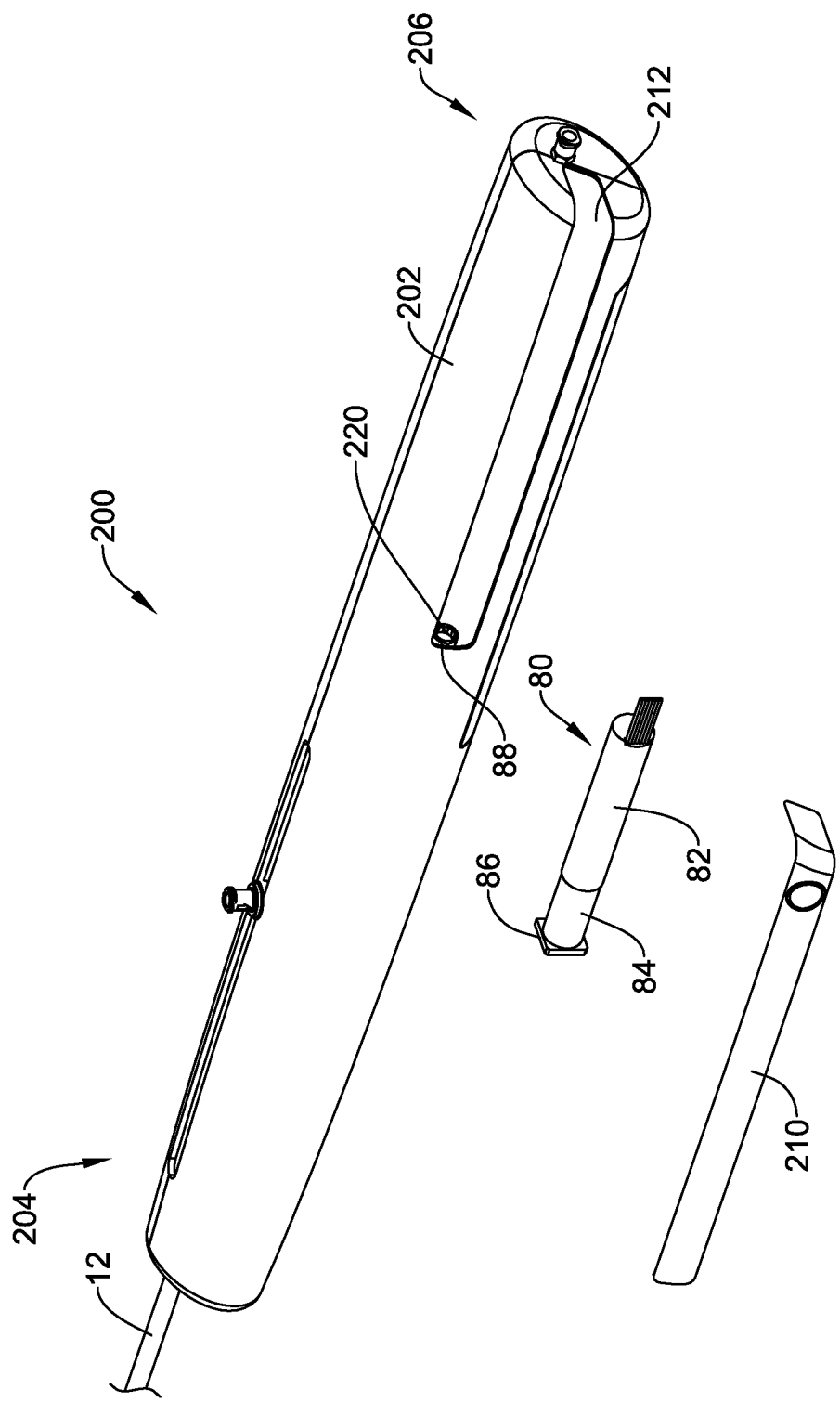
FIG. 11 is a partially exploded view of the example medical device system of FIG. 9.
Figure 11A:
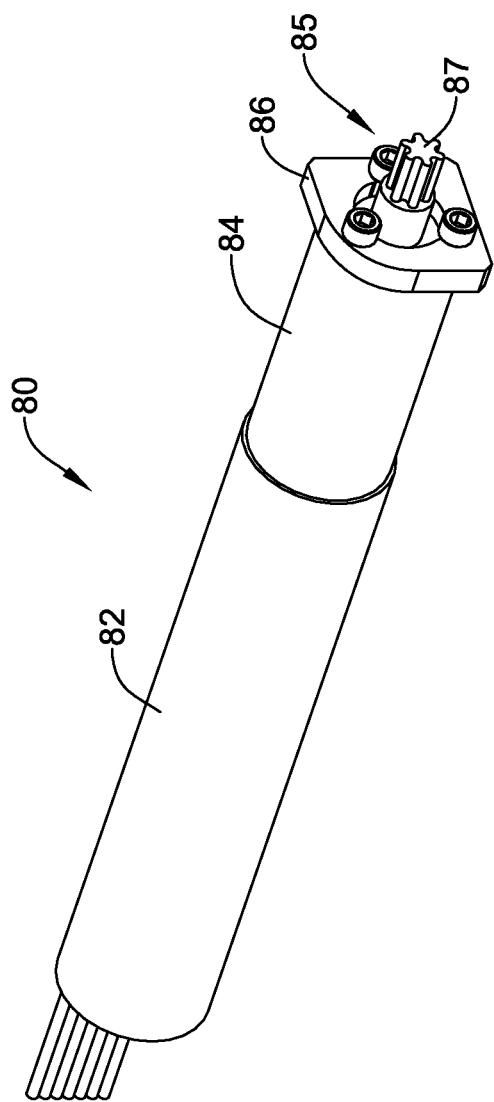
FIG. 11A is a perspective view of a portion of the example medical device system of FIG. 11.

As can be seen in FIG. 11A, the outer sheath assembly drive motor 80 includes a keyed driveshaft that is configured to engage a correspondingly keyed aperture formed within an end of the outer sheath assembly threaded rod 88. In some cases, as illustrated, the outer sheath assembly drive motor 80 includes a splined driveshaft 87 that is configured to slidingly engage a corresponding splined aperture 220 formed within an end of the outer sheath assembly threaded rod 88. In other cases, differing keyed features may be used. For example, the outer sheath assembly drive motor 80 may have a keyed driveshaft emulating an Allen wrench, while the aperture 220 has a similarly keyed configuration.

Figure 12:
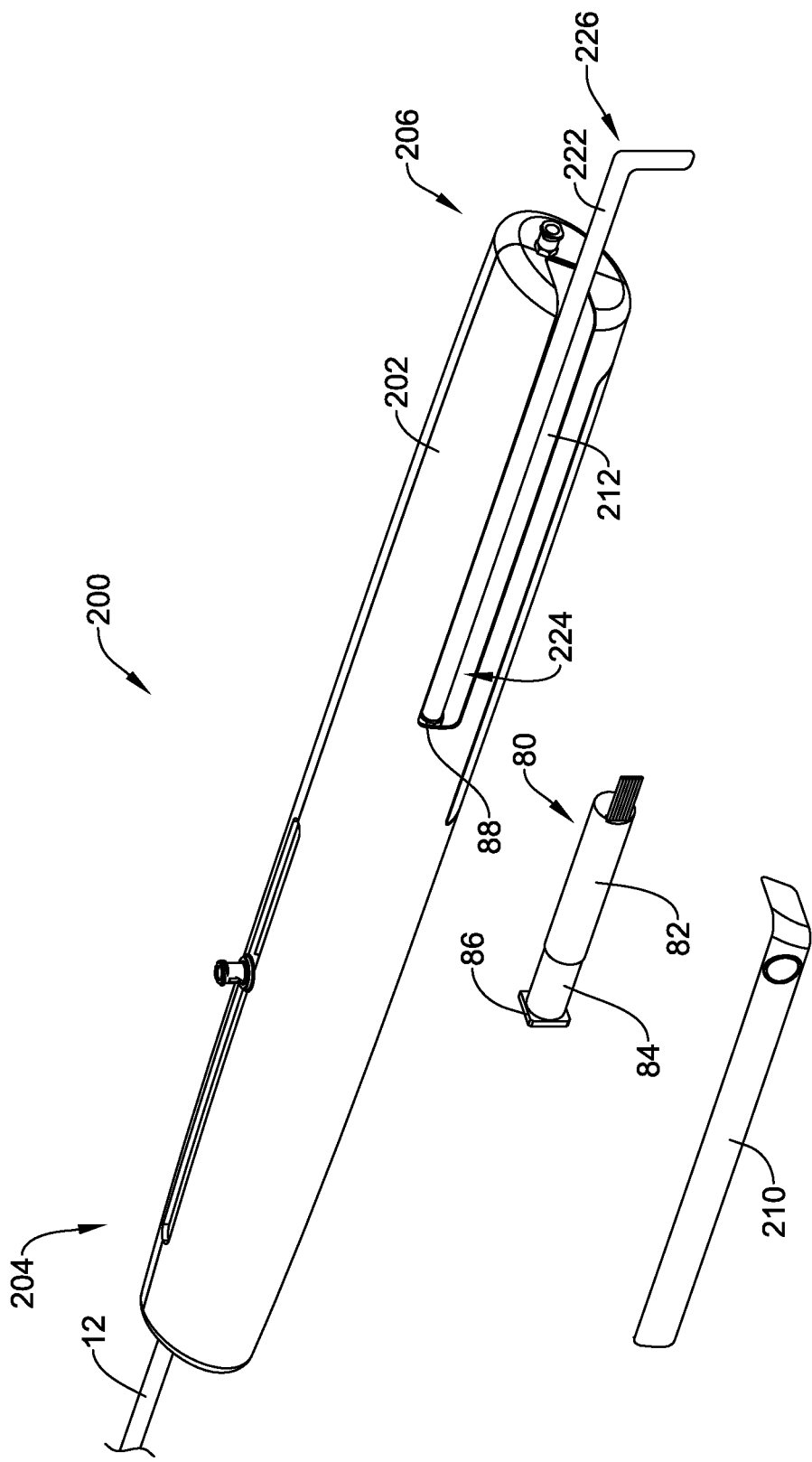
FIG. 12 is a partially exploded view of the example medical device system of FIG. 9.

As seen in FIG. 12, a manual drive tool such as an outer sheath drive tool 222 having an engagement end 224 and a handle end 226 may be used to manually actuate the outer sheath drive assembly 74 by inserting the engagement end 224 into the splined aperture 220 and rotating the outer sheath drive tool 222 using the handle end 226. While a splined aperture 220 is shown, it will be appreciated that any number of engagement features between the outer sheath motor coupling 86 and the outer sheath assembly drive motor 80 (and hence between the outer sheath motor coupling 86 and the engagement end 224 of the outer sheath drive tool 222) may be utilized. In some cases, the outer sheath drive tool 222 may be stored within the outer sheath cavity 212, and in some cases may be secured to a snap-fitting on an interior surface of the outer sheath access door 210. In some cases, the outer sheath drive tool 222 may instead be stored separately, such as within the packaging that the system 10 is provided in. As a result of removing the outer sheath assembly drive motor 80 and utilizing the outer sheath drive tool 222, the outer sheath 12 may be advanced or withdrawn relative to the implantable medical device 16.

Figure 13:
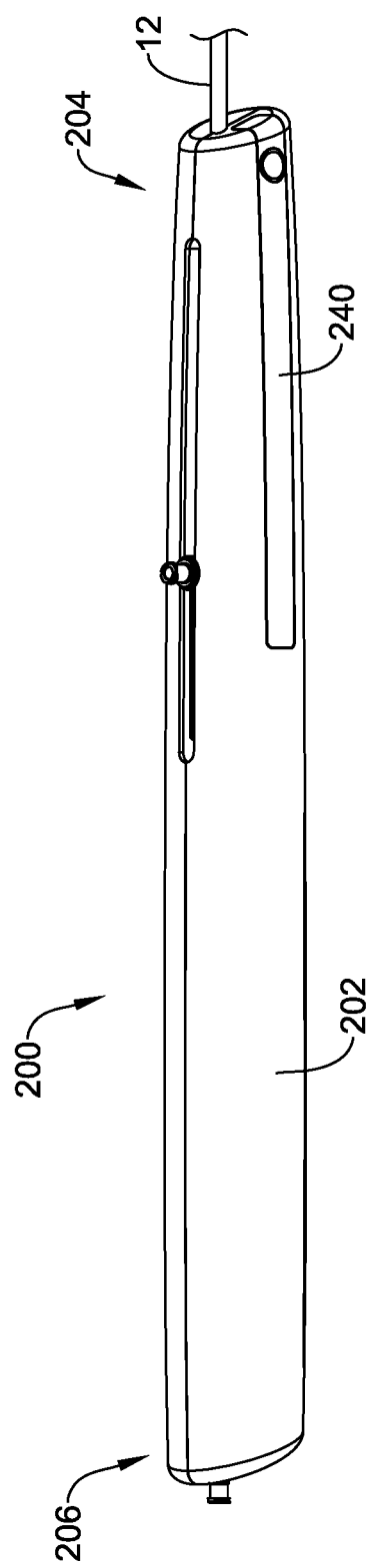
FIG. 13 is a partially exploded view of the example medical device system of FIG. 9.
Figure 14:
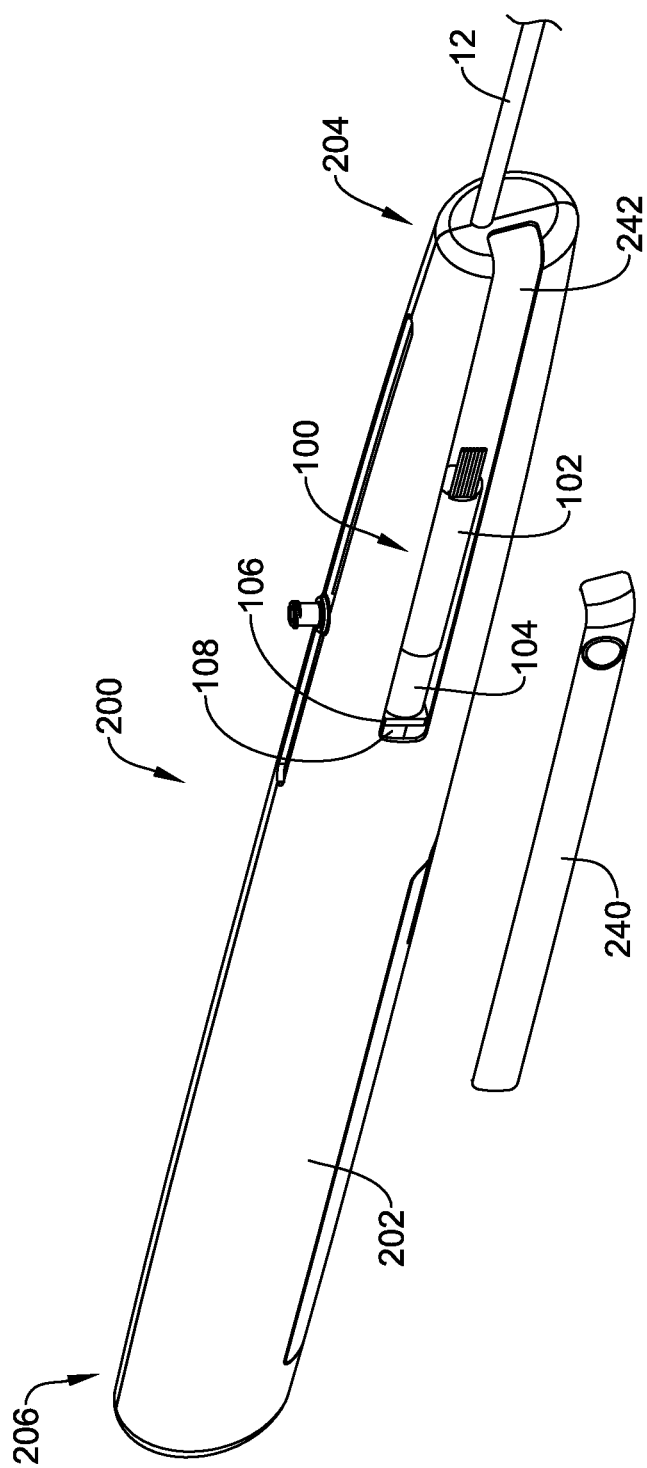
FIG. 14 is a partially exploded view of the example medical device system of FIG. 9.
Figure 15:
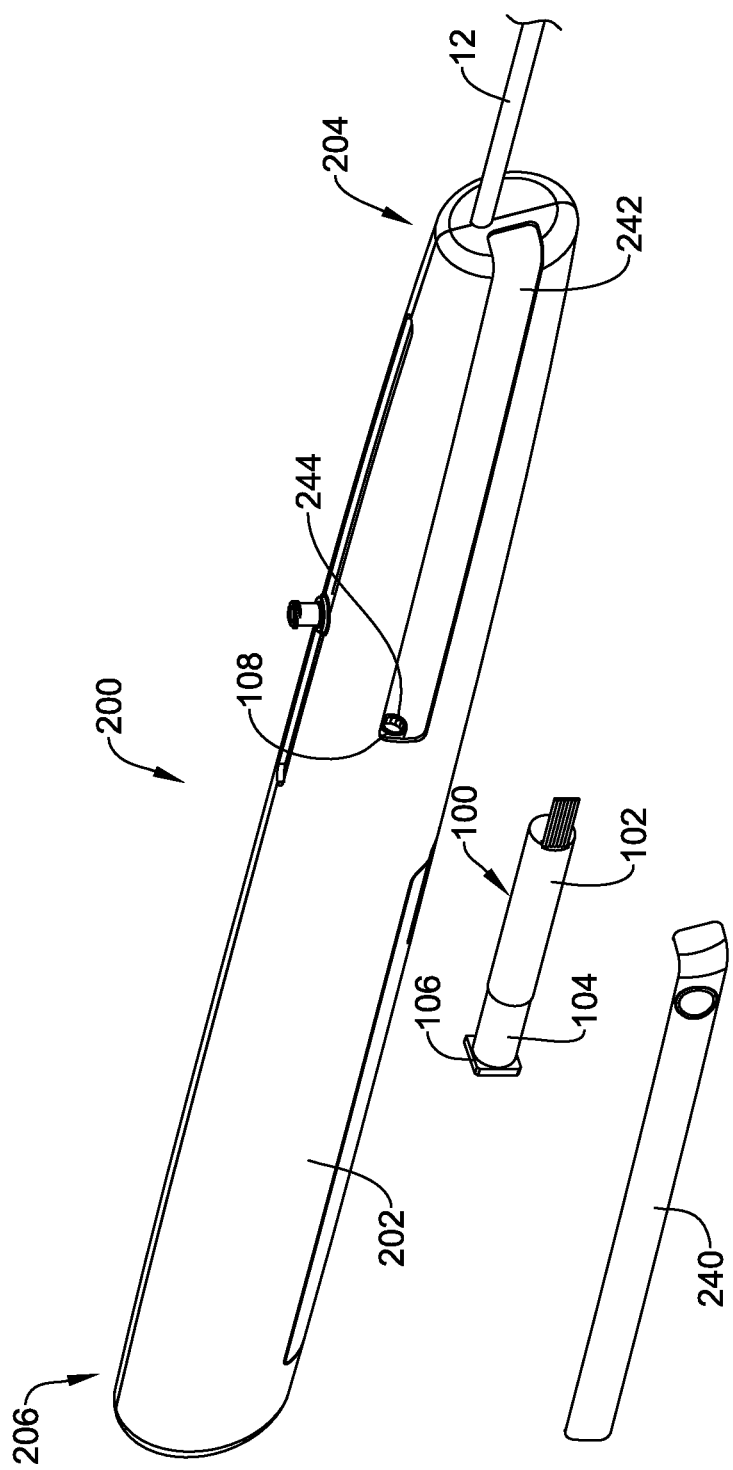
FIG. 15 is a partially exploded view of the example medical device system of FIG. 9.

FIG. 13 shows an opposing side of the medical device system 200. While the previous FIGS. illustrated a way in which the outer sheath assembly drive motor 80 could be removed and the outer sheath 12 manually advanced, for example, in some cases there may be a desire to remove the actuation shaft assembly drive motor 100 such that the actuation shaft drive assembly threaded rod 108 may be manually actuated. As seen in FIG. 13, the handle 202 includes an actuation shaft access door 240. In some cases, the actuation shaft access door 240 may have a snap-fit connection to the handle 202, or may be attached and/or removed in any desired manner. Removing the actuation shaft access door, as shown for example in FIG. 14, reveals an outer sheath cavity 242, with the actuation shaft assembly drive motor 100. Also visible in FIG. 14 is the actuation shaft motor coupling 106, which enables the actuation shaft drive assembly motor 100 to engage the actuation shaft drive assembly threaded rod 108.

If necessary, such as in the case of power loss, motor failure, or other mechanical failures, the actuation shaft assembly drive motor 100 may be removed once the actuation shaft door 240 has been removed from the handle 202. This can be seen for example in FIG. 15, where both the actuation shaft access door 240 as well as the actuation shaft assembly drive motor 100 has been removed from the handle 202. In some cases, the actuation shaft assembly drive motor 100 may be held against translational movement by a fixation feature present within the outer sheath cavity 212, and the actuation shaft assembly drive motor 100 may be released from the fixation feature by sliding the actuation shaft assembly drive motor 100 axially away from the fixation feature.

Figure 16:
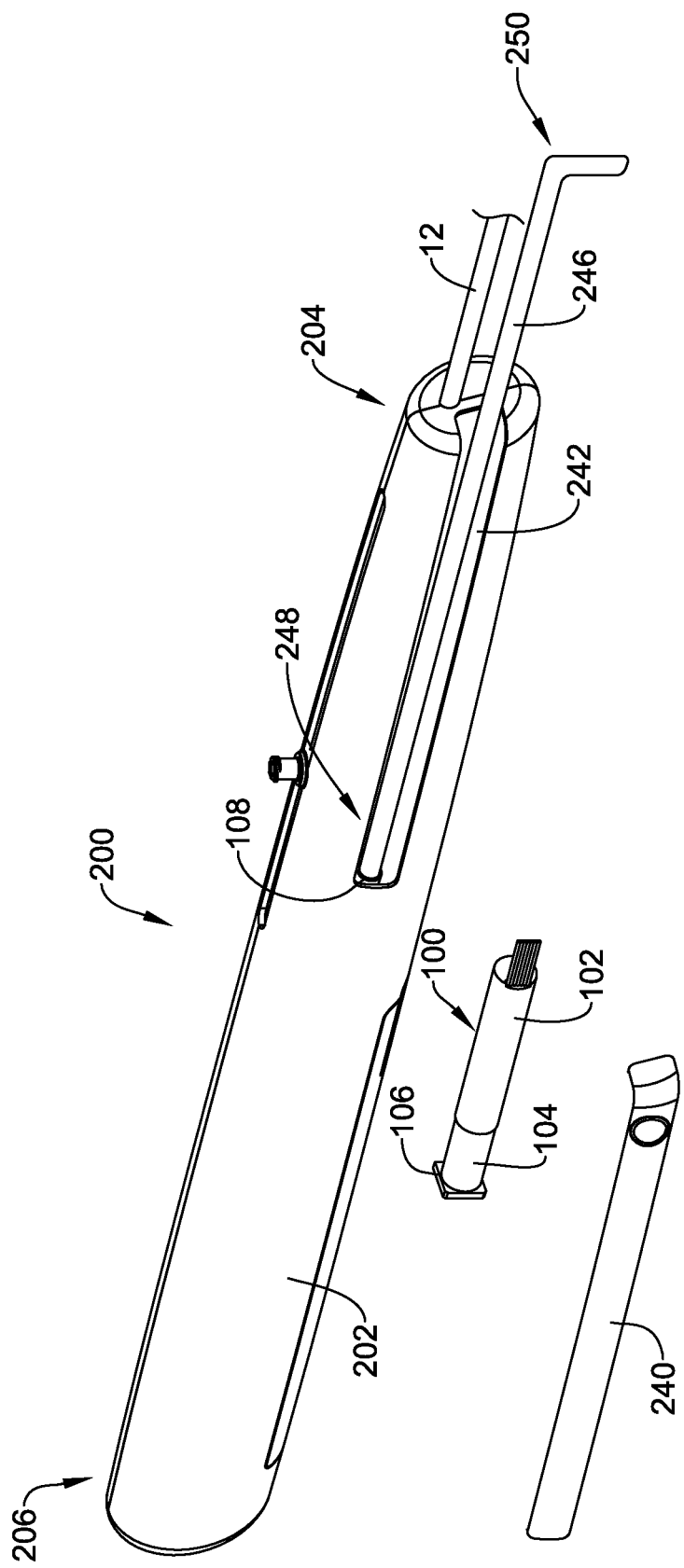
FIG. 16 is a partially exploded view of the example medical device system of FIG. 9.

As can be seen, the actuation shaft motor coupling 106 includes a splined aperture 244. As seen in FIG. 16, a manual drive tool such as an actuation shaft drive tool 246 having an engagement end 248 and a handle end 250 may be used to manually actuate the actuation shaft drive assembly 76 by inserting the engagement end 248 into the splined aperture 244 and rotating the actuation shaft drive tool 246 using the handle end 250. While a splined aperture 244 is shown, it will be appreciated that any number of engagement features between the actuation shaft motor coupling 106 and the actuation shaft assembly drive motor 100 (and hence between the actuation shaft motor coupling 106 and the engagement end 248 of the outer sheath drive tool 246) may be utilized. In some cases, the actuation shaft drive tool 246 may be stored within the actuation shaft cavity 242, and in some cases may be secured to a snap-fitting on an interior surface of the actuation shaft access door 240 or stored within the packaging. As a result of removing the actuation shaft assembly drive motor 100 and utilizing the actuation shaft drive tool 246, the actuation shaft 30 may be advanced or withdrawn relative to the implantable medical device 16.

Figure 17:
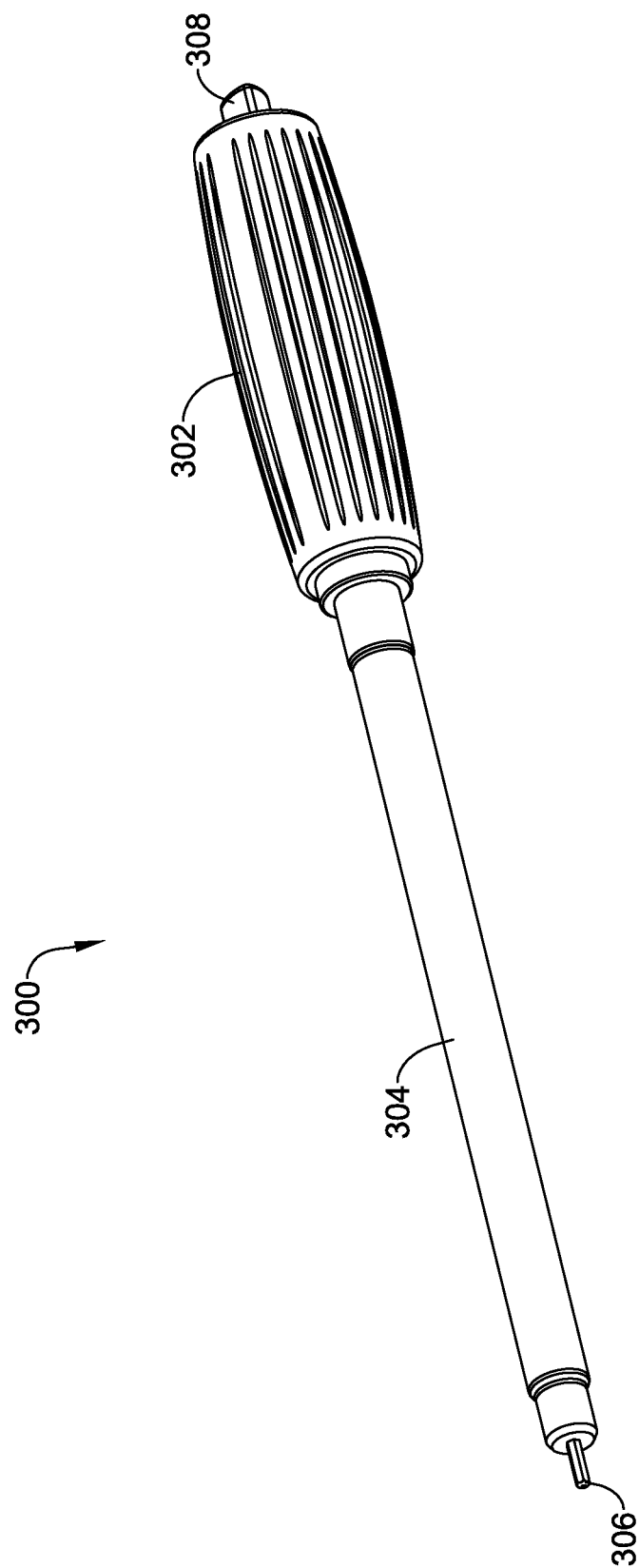
FIG. 17 is a perspective view of an example manual drive tool.

FIG. 17 is a perspective view of another manual drive tool 300 that may, for example, be used as the outer sheath drive tool 222 and/or the actuation shaft drive tool 246. As noted, there is a keyed relationship between the manual drive tool 300 and the particular threaded rod that the manual drive tool 300 is intended to engage. In some cases, as shown, the manual drive tool 300 includes a handle portion 302 that is coupled with an elongate member 304 terminating in a keyed portion 306. In some cases, there is a splined relationship. In some cases, as illustrated, the keyed portion 306 forms an Allen wrench. These are just examples, as any variety of different keyed shaped could be used. In some cases, the manual drive tool 300 may include an access door key 308 that may be used to engage and remove an access door, as will be shown in FIG. 18.

Figure 18:
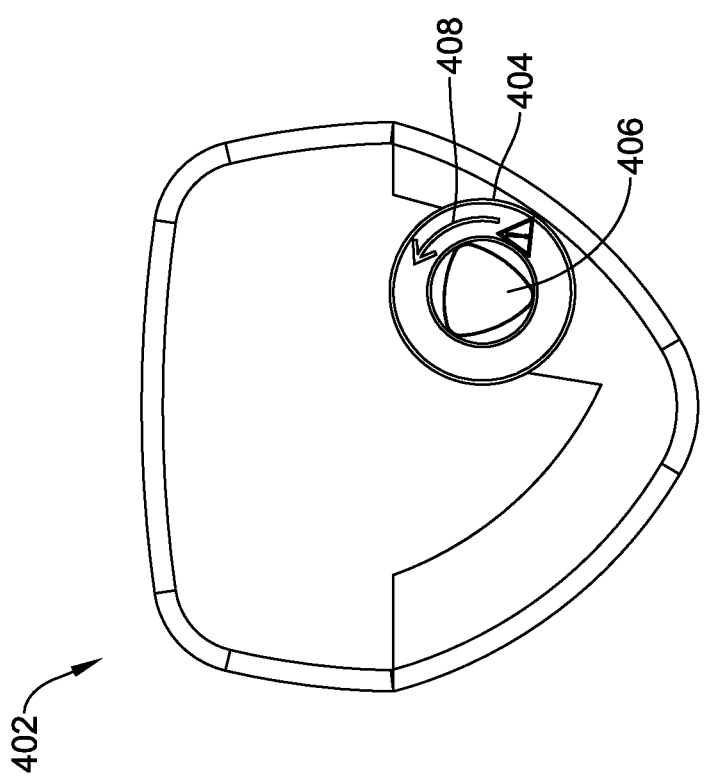
FIG. 18 is a proximal end view of an example medical device system.

In some cases, a drive motor such as the outer sheath drive assembly motor 80 may not be removed out the side of the handle 202, but rather may be removed out a proximally located door. FIG. 18 is a proximal end view of a handle 402 that may be considered as being similar to the handle 202 discussed previously, apart from a change in where an access door 404 is located. In some cases, the access door 404 may be threadedly engaged with the handle 402. In some cases, if there is a need to access the outer sheath drive assembly motor 80, the access door 404 may be removed by inserting an appropriate tool such as the access door key 308 (forming part of the manual drive tool 300) into a correspondingly shaped recess 406 formed within the access door 404. In some cases, the access door 404 may include an arrow or other indicia 408 indicating which direction the access door 404 should be turned in order to remove the access door 404.

Figure 19:
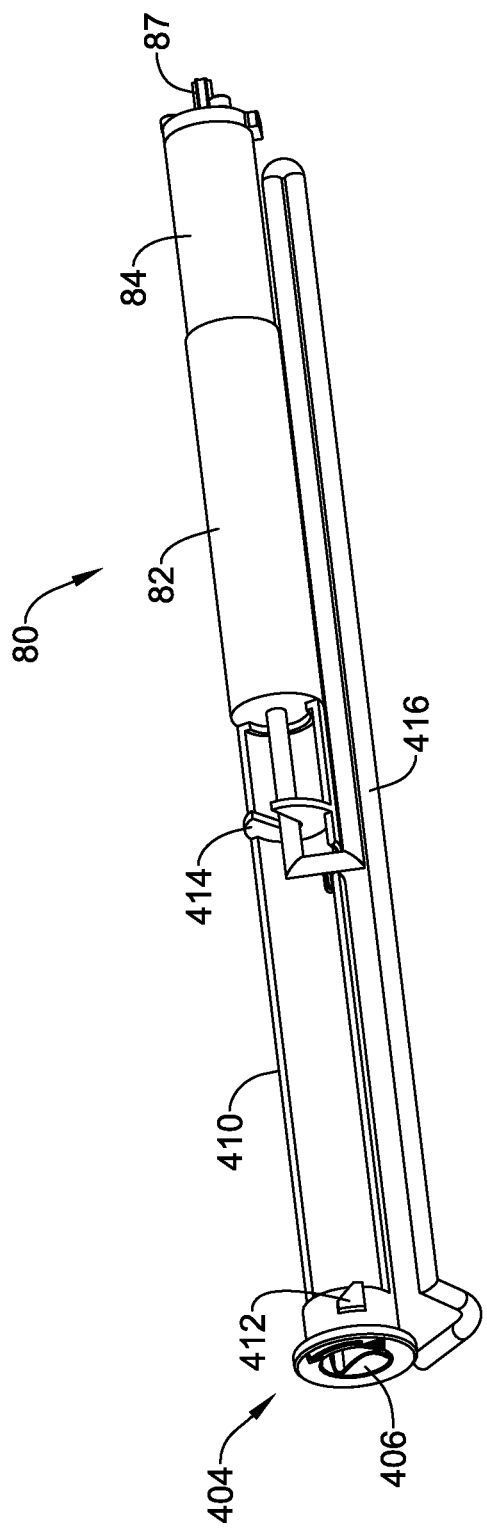
FIG. 19 is a perspective view of a portion of the example medical device system of FIG. 18.

In some cases, once the access door 404 has been removed, a user may be able to withdraw the access sheath assembly drive motor 80 in a subsequent step. In some cases, as shown for example in FIG. 19, the access sheath assembly drive motor 80 may be coupled with a motor carrier 410. In some cases, the motor carrier 410 may be coupled with the access sheath assembly drive motor 80 such that by withdrawing the motor carrier 410, the access sheath assembly drive motor 80 may also be removed. As illustrated, the motor carrier 410 may be integrally formed with the access door 404. As a result, rotating and removing the access door 404 enables the user to withdraw the motor carrier 410 and the access sheath assembly drive motor 80 as an assembly. It will be appreciated that in some instances, the motor carrier 410 may have a rotatable coupling to the access sheath assembly drive motor 80 that allows the motor carrier 410 to rotate relative to the access sheath assembly drive motor 80.

In some cases, the access door 404 may include one or two or more pegs 412 that engage the handle 402 in order to secure the access door 404 in position relative to the handle 402 yet allow the access door 404 to be rotated out of engagement with the handle 402. In some instances, the access door 404 may instead include one or more threads that engages corresponding threads formed within the handle 402 to rotatably secure the access door 404 in place. In some cases, while not illustrated, the access door 404 may include an O-ring to prevent inadvertent fluid entrance into the handle 402 when the access door 404 is in a closed position relative to the handle 402. In some instances, as illustrated, the motor carrier 410 may include a wiring feature 414 that helps to locate wiring 416 that powers the access sheath assembly drive motor 80.

Once the access door 404, the motor carrier 410 and the access sheath assembly drive motor 80 have been removed, a tool such as the manual drive tool 300 (FIG. 17) may be used to engage the outer sheath drive assembly threaded rod 88. It will be appreciated that the manual drive tool 300 includes a keyed portion 306 that matches a shape of the driveshaft on the access sheath assembly drive motor 80. While in some cases the access sheath assembly drive motor 80 has been shown with a splined driveshaft 87, as illustrated the access sheath assembly drive motor 80 may have a keyed driveshaft 87' having an Allen wrench configuration.

Figure 20:
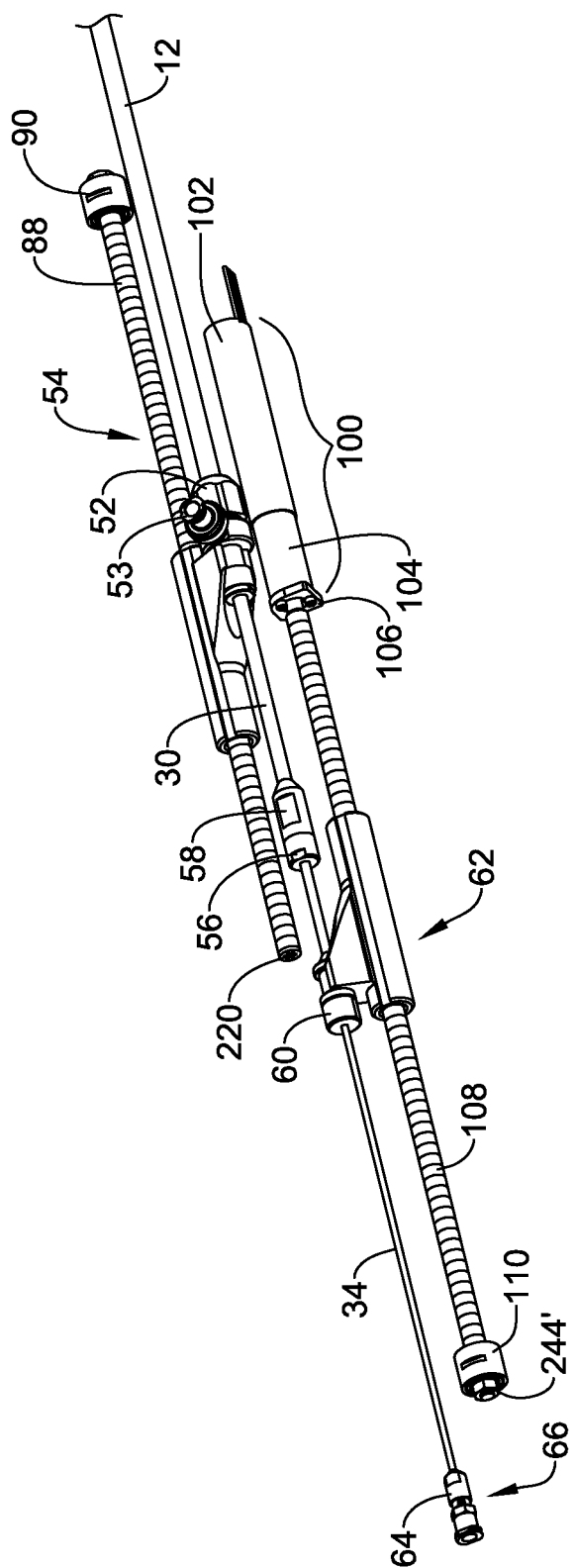
FIG. 20 is a partially exploded view of the example medical device system of FIG. 18.

In some cases, there may be a desire to manually actuate the outer sheath drive assembly threaded rod 88 and the actuation shaft drive assembly threaded rod 108. FIG. 20 is similar to FIG. 5, but the access sheath assembly drive motor 80 (and motor carrier 410 if present) has been removed. With removal of the access sheath assembly drive motor 80, the keyed or splined aperture 220 formed within an end of the access sheath assembly threaded rod 88 is accessible. Also accessible is a keyed or splined aperture 244' formed in an end of the actuation shaft drive assembly threaded rod 108. In some cases, the actuation shaft assembly drive motor 100 may be separately removed, or may be left in place. In some cases, the actuation shaft drive assembly threaded rod 108 may be manually driven against the actuation shaft drive motor 100 if the actuation shaft drive motor 100 is not removed or mechanically disengaged from the actuation shaft drive assembly threaded rod 108.

Figure 21:
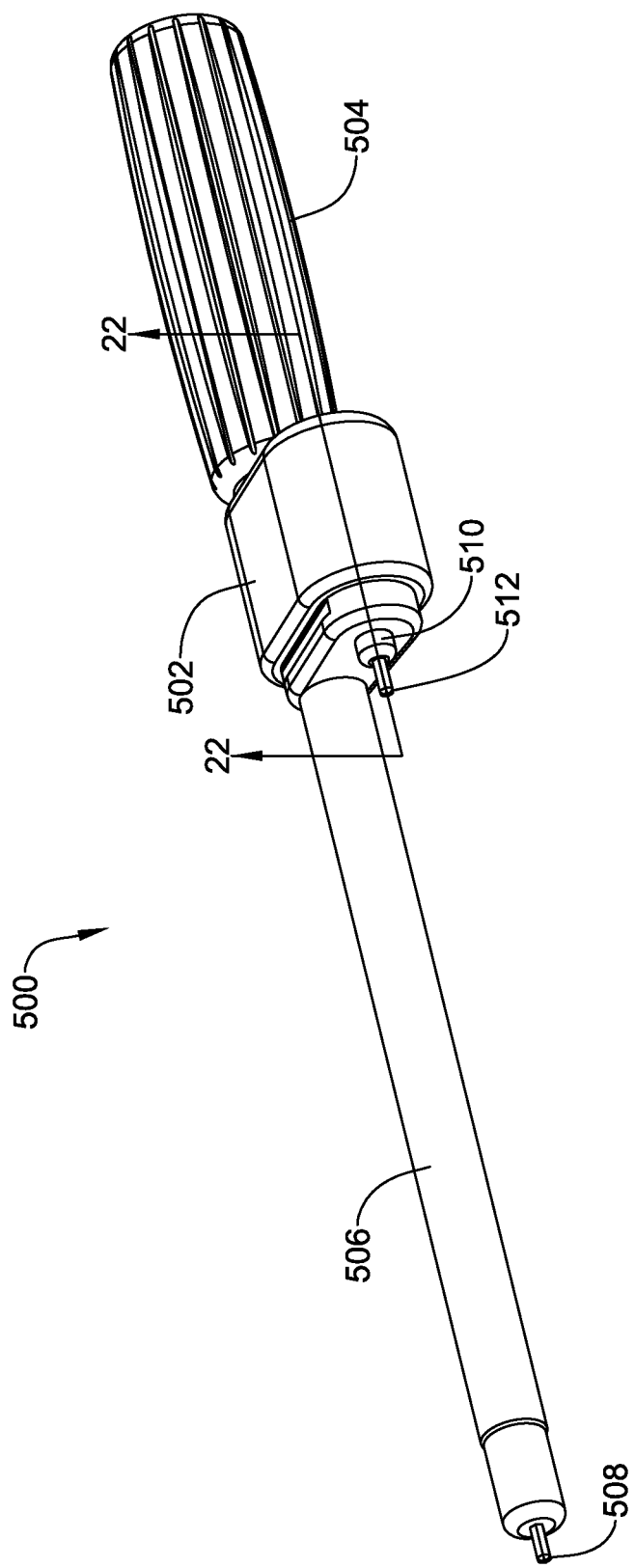
FIG. 21 is a perspective view of an example manual drive tool.
Figure 22:
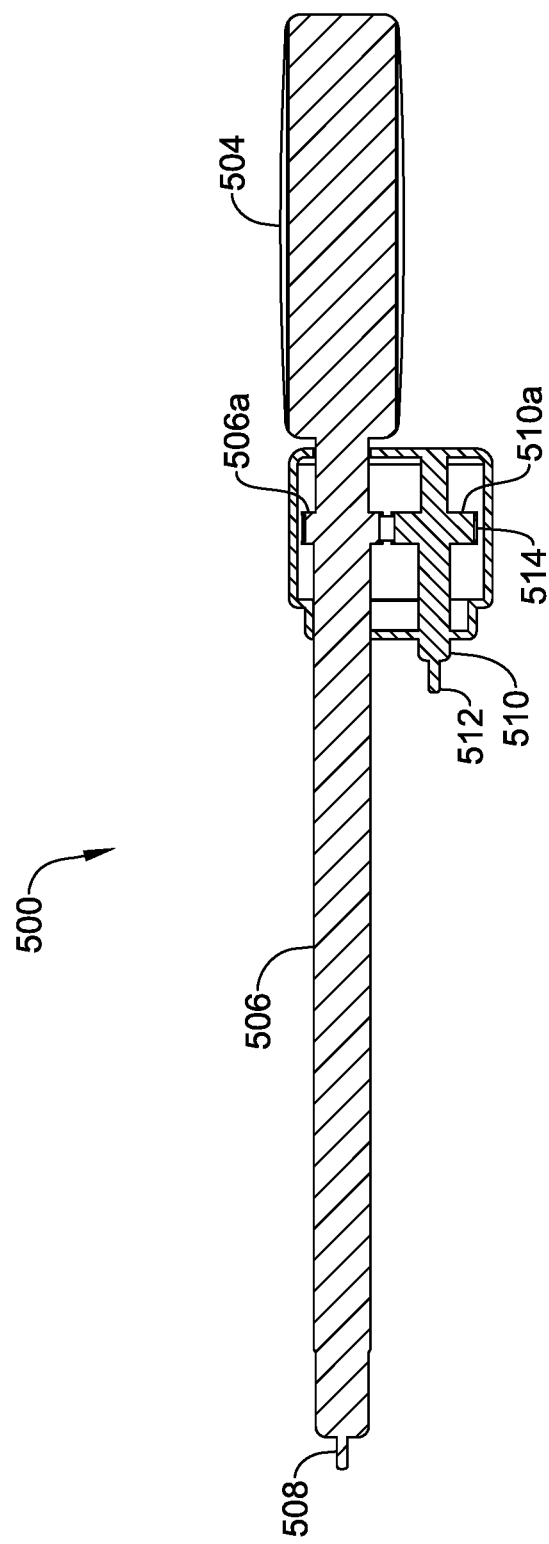
FIG. 22 is a partial cross-sectional view of a portion of the example medical device system of FIG. 18.

FIG. 21 is a perspective view of a manual drive tool 500 that may be used to drive both the outer sheath drive assembly threaded rod 88 and the actuation shaft drive assembly threaded rod 108 simultaneously. FIG. 22 is a cross-section of the manual drive tool 500, taken along line 22-22 of FIG. 21. The manual drive tool 500 includes a body 502 and a handle 504 that is rotatably secured relative to the handle 504. As the handle 504 is turned, an outer sheath drive shaft 506 rotates in turn. The outer sheath drive shaft 506 is configured to rotatably engage the outer sheath drive assembly threaded rod 88 in place of the outer sheath assembly drive motor 80, and thus includes a keyed portion 508 that is complementary to the keyed or splined aperture 220 formed within the outer sheath drive assembly threaded rod 88. The manual drive tool 500 also includes an actuation shaft drive shaft 510 that is configured to rotatably engage the actuation shaft drive assembly threaded rod 108. The actuation shaft drive shaft 510 includes a keyed portion 512 that is complementary to the keyed or splined aperture 244' formed in an end of the actuation shaft drive assembly threaded rod 108.

As can be seen in FIG. 22, the outer sheath drive shaft 506 includes a drive wheel 506*a* and the actuation shaft drive shaft 510 includes a drive wheel 510*a*. As illustrated, a belt or chain 514 extends between the drive wheel 506*a* and the drive wheel 510*a*. It will be appreciated that the relative rotation speed of the actuation shaft drive shaft 510 and the outer sheath drive shaft 506 may be adjusted or otherwise controlled by varying the relative diameters of the drive wheel 506*a* and the drive wheel 510*a*. In some cases, instead of a belt or chain 514, one or more intervening gears may be used instead. In comparing FIG. 21 with FIG. 20, it will be appreciated that the relative lengths of the outer sheath drive shaft 506 and the actuation shaft drive shaft 510 correspond to the relative axial positions of the keyed or splined aperture 220 formed within an end of the access sheath assembly threaded rod 88 and the keyed or splined aperture 244' formed in an end of the actuation shaft drive assembly threaded rod 108.

The materials that can be used for the various components of the medical devices and/or systems 10 and 200 disclosed herein may include those commonly associated with medical devices. However, this is not intended to limit the devices and methods described herein, as the discussion may be applied to other components of the medical devices and/or systems 10, 200 disclosed herein including the various shafts, liners, components described relative thereto.

The medical device 10, 200 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10, 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10, 200 to achieve the same result.

In some embodiments, a degree of Magnetic Resonance Imaging (MRI) compatibility is imparted into the medical device 10, 200. For example, the medical device 10, 200 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable medical device, comprising:
a handle housing extending from a proximal region to a distal region;
an outer sheath access door disposed near the proximal region;
an outer sheath configured to cover at least a portion of the implantable medical device, the outer sheath extending distally from the handle housing;
an outer sheath coupler disposed within the handle housing and secured to the outer sheath;
an outer sheath nut threadedly disposed on an outer sheath threaded rod and operably coupled to the outer sheath coupler; and
an outer sheath drive motor operably coupled to the outer sheath threaded rod such that actuation of the outer sheath drive motor causes the outer sheath threaded rod to rotate relative to the outer sheath nut, thereby causing the outer sheath nut to translate relative to the outer sheath threaded rod as the outer sheath nut is held against rotation, and thus causing the outer sheath coupler and the outer sheath to translate relative to the handle housing;
wherein the outer sheath drive motor is configured to be disengaged from the outer sheath threaded rod upon removal of the outer sheath access door such that a manual drive tool can be used to engage and manually rotate the outer sheath threaded rod.

2. The system of claim 1, wherein the outer sheath threaded rod comprises a keyed aperture at an end thereof, and the outer sheath drive motor comprises a keyed drive shaft that is complementary to the keyed aperture and is slidingly engageable therewith.

3. The system of claim 2, wherein the keyed aperture comprises a splined aperture, and the keyed drive shaft comprises a splined drive shaft.

4. The system of claim 1, wherein the outer sheath access door extends along a side of the handle housing such that removal of the outer sheath access door exposes at least a portion of a length of the outer sheath drive motor.

5. The system of claim 4, wherein the outer sheath access door has a snap-fit connection with the handle housing.

6. The system of claim 1, wherein the outer sheath access door is disposed on a proximal end of the handle housing.

7. The system of claim 6, further comprising a motor carrier operably coupled to the outer sheath drive motor such that removal of the motor carrier through the outer sheath access door removes the outer sheath drive motor.

8. The system of claim 7, wherein the motor carrier is operably coupled to the outer sheath access door such that removal of the outer sheath access door removes the motor carrier from within the handle housing.

9. The system of claim 1, further comprising:
an actuation shaft access door;
an actuation shaft extending within the outer sheath;
an actuation shaft coupler secured to the actuation shaft such that translation of the actuation shaft coupler relative to the handle housing causes translation of the actuation shaft relative to the handle housing; an actuation shaft nut threadedly disposed on an actuation shaft threaded rod and operably coupled to the actuation shaft coupler;
an actuation shaft drive motor operably coupled to the actuation shaft threaded rod such that actuation of the actuation shaft drive motor causes the actuation shaft threaded rod to rotate relative to the actuation shaft nut, thereby causing the actuation shaft nut to translate relative to the actuation shaft threaded rod as the actuation shaft nut is held against rotation, and thus causes the actuation shaft coupler and the actuation shaft to translate relative to the handle housing;
wherein the actuation shaft drive motor is configured to be disengaged from the actuation shaft threaded rod upon removal of the actuation shaft access door such that the manual drive tool can be used to manually rotate the actuation shaft threaded rod.

10. The system of claim 9, wherein the actuation shaft threaded rod comprises a keyed aperture at an end thereof, and the actuation shaft drive motor comprises a keyed drive shaft that is complementary to the keyed aperture and is slidingly engageable therewith.

11. The system of claim 10, wherein the keyed aperture comprises a splined aperture, and the keyed drive shaft comprises a splined drive shaft.

12. The system of claim 10, wherein the actuation shaft access door extends along a side of the handle housing such that removal of the actuation shaft access door exposes at least a portion of a length of the actuation shaft drive motor.

13. The system of claim 9, wherein the actuation shaft access door has a snap-fit connection with the handle housing.

14. A system for delivering an implantable medical device, comprising:
a handle housing, the handle housing including an outer sheath access door;
an outer sheath configured to cover at least a portion of the implantable medical device;
an outer sheath coupler secured to the outer sheath such that translation of the outer sheath coupler relative to the handle housing causes translation of the outer sheath relative to the handle housing;
a threaded rod;
an outer sheath nut threadedly disposed on the threaded rod and operably coupled to the outer sheath coupler;
an outer sheath drive motor operably coupled to the threaded rod such that actuation of the outer sheath drive motor causes the threaded rod to rotate relative to the outer sheath nut, thereby causing the outer sheath nut to translate relative to the threaded rod as the outer sheath nut is held against rotation, and thus causes the outer sheath coupler and the outer sheath to translate relative to the handle housing;
the outer sheath drive motor configured to be disengaged from the threaded rod upon removal of the outer sheath access door; and
an outer sheath drive tool having an engagement end and a handle end, the engagement end configured to engage the threaded rod once the outer sheath drive motor has been removed so that the threaded rod can be manually rotated.

15. The system of claim 14, wherein the threaded rod comprises a keyed aperture at an end thereof, and the outer sheath drive motor comprises a keyed drive shaft that is complementary to the keyed aperture and is slidingly engageable therewith.

16. The system of claim 15, wherein the keyed aperture comprises a splined aperture, and the keyed drive shaft comprises a splined drive shaft.

17. A system for delivering an implantable medical device, comprising:
- a handle housing, the handle housing including an access door;
- an outer sheath configured to cover at least a portion of the implantable medical device, the outer sheath extending distally from the handle housing;
- an outer sheath coupler disposed within the handle housing and secured to the outer sheath;
- an outer sheath nut threadedly disposed on an outer sheath threaded rod and operably coupled to the outer sheath coupler;
- an outer sheath drive motor operably coupled to the outer sheath threaded rod such that actuation of the outer sheath drive motor causes the outer sheath threaded rod to rotate relative to the outer sheath nut, thereby causing the outer sheath nut to translate relative to the outer sheath threaded rod as the outer sheath nut is held against rotation, and thus causing the outer sheath coupler and the outer sheath to translate relative to the handle housing;
- an actuation shaft operably coupled to translation members secured relative to the implantable medical device such that translation of the actuation shaft causes translation of the translation members which in turn causes the implantable medical device to shift from a delivery configuration to a deployment configuration, the actuation shaft extending within the outer sheath;
- an actuation shaft coupler secured to the actuation shaft such that translation of the actuation shaft coupler relative to the handle housing causes translation of the actuation shaft relative to the handle housing;
- an actuation shaft nut threadedly disposed on an actuation shaft threaded rod and operably coupled to the actuation shaft coupler;
- an actuation shaft drive motor operably coupled to the actuation shaft threaded rod such that actuation of the actuation shaft drive motor causes the actuation shaft threaded rod to rotate relative to the actuation shaft nut, thereby causing the actuation shaft nut to translate relative to the actuation shaft threaded rod as the actuation shaft nut is held against rotation, and thus causes the actuation shaft coupler and the actuation shaft to translate relative to the handle housing;
- wherein removal of the access door enables removal of the outer sheath drive motor.

18. The system of claim 17, further comprising a manual drive tool including an outer sheath drive shaft configured to rotatably engage the outer sheath threaded rod in place of the outer sheath drive motor and an actuation shaft drive shaft configured to rotatably engage the actuation shaft threaded rod at an end thereof opposite that of the actuation shaft drive motor.

19. The system of claim 18, wherein the manual drive tool is configured to maintain a drive ratio between the outer sheath drive shaft and the actuation shaft drive shaft.

20. The system of claim 17, wherein the access door is configured to be manually removed from the handle housing.

* * * * *